United States Patent [19]

Vazquez et al.

[11] Patent Number: 5,583,132
[45] Date of Patent: Dec. 10, 1996

[54] SULFONYLALKANOYLAMINO HYDROXYETHYLAMINO SULFAMIC ACIDS USEFUL AS RETROVIRAL PROTEASE INHIBITORS

[76] Inventors: Michael L. Vazquez, 233 Saratoga Ct., Gurnee, Ill. 60031; Richard A. Mueller, 562 Stonegate Ter., Glencoe, Ill. 60022; John J. Talley, 1079 Darwick Ct., St. Louis, Mo. 63132; Daniel P. Getman, 66 Sunnyhill Ct., Chesterfield, Mo. 63017; Gary A. DeCrescenzo, 536 Schrader Farm Dr., St. Peters, Mo. 63376; Eric T. Sun, 7614 Palmilla Dr. Apt. 58, San Diego, Calif. 92212

[21] Appl. No.: 379,645
[22] PCT Filed: Oct. 29, 1993
[86] PCT No.: PCT/US93/10461
§ 371 Date: Feb. 2, 1995
§ 102(e) Date: Feb. 2, 1995
[87] PCT Pub. No.: WO94/10136
PCT Pub. Date: May 11, 1994
[51] Int. Cl.$^6$ .......... C07C 307/02; A61K 31/18; A61K 31/40; A61K 31/535
[52] U.S. Cl. .......... 514/183; 540/482; 540/604; 544/160; 544/383; 546/309; 546/336; 546/337; 548/542; 548/950; 549/68; 549/480; 560/13; 560/150; 562/427; 562/430; 562/470
[58] Field of Search .......... 544/160, 383; 514/238.2, 600, 539, 541, 329, 352, 357, 562, 210, 424, 447, 472, 183, 212, 255; 564/79, 78; 560/13; 546/309, 336, 337; 540/482, 604; 548/542, 950; 549/68, 480; 562/472, 430

[56] References Cited

U.S. PATENT DOCUMENTS

| H725 | 1/1990 | Gordon | 548/533 |
|---|---|---|---|
| 4,450,164 | 5/1984 | Bristol et al. | 424/256 |
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,599,198 | 7/1986 | Hoover | 260/998.2 |
| 4,616,088 | 10/1986 | Ryono et al. | 546/336 |
| 4,668,770 | 5/1987 | Boger et al. | 530/331 |
| 4,688,769 | 5/1987 | Hoover | 530/331 |
| 4,757,050 | 7/1988 | Natarajan et al. | 514/18 |
| 4,880,938 | 11/1989 | Freidinger | 548/492 |
| 4,963,530 | 10/1990 | Hemmi et al. | 514/19 |
| 4,977,277 | 12/1990 | Rosenberg et al. | 549/215 |

FOREIGN PATENT DOCUMENTS

| 79823/87 | 4/1988 | Australia | C07K 5/06 |
|---|---|---|---|
| 104041 | 3/1984 | European Pat. Off. | C07C 103/52 |
| 114993 | 8/1984 | European Pat. Off. | C07C 103/52 |
| 172347 | 2/1986 | European Pat. Off. | C07K 5/00 |
| 223437 | 5/1987 | European Pat. Off. | C07K 5/00 |
| 0264795 | 4/1988 | European Pat. Off. | C07K 5/00 |
| 337714 | 10/1989 | European Pat. Off. | C07K 5/02 |
| 0342541 | 11/1989 | European Pat. Off. | C07K 5/02 |
| 0346847 | 12/1989 | European Pat. Off. | C07D 207/10 |
| 356223 | 2/1990 | European Pat. Off. | C07K 37/64 |
| 364804 | 4/1990 | European Pat. Off. | |
| 389898A2 | 10/1990 | European Pat. Off. | C07K 5/02 |
| 393445 | 10/1990 | European Pat. Off. | A61K 37/64 |
| 468641 | 1/1992 | European Pat. Off. | |
| 2184730 | 7/1987 | United Kingdom | C07K 5/00 |
| 2200115 | 7/1988 | United Kingdom | C07C 103/00 |
| 2209752 | 5/1989 | United Kingdom | C07C 103/30 |
| WO84/03044 | 8/1984 | WIPO | A61K 37/64 |
| 94/05639 | 3/1994 | WIPO | |
| 94/04493 | 3/1994 | WIPO | |

OTHER PUBLICATIONS

Roberts et al, "Rational Design of Peptide–based Proteinase Inhibitors," Science, 248, 358 (1990).
Erickson et al, "Design Activity, and 2.8Å Crystal Structure of a $C_2$ Symmetric Inhibitor Complexed to HIV–1 Protease," Science, 249, 527 (1990).
Pearl et al, "Sequence specificity of retroviral proteases" Nature, 328, p. 482 (1987).
Martin, Drugs of the Future, 16(3), 210–212 (1991).
Meek et al, *Letter To Nature*, 343, 90–92 (1990).
McQuade et al, *Science*, 274, 454–456 (1990).
Rich et al, Peptide Inhibitors of Proteases, 511–520, Year Not Available.
Rosenberg et al, *J. Med. Chem.*, 30, 1224–1228 (1987).

*Primary Examiner*—Johann Richter
*Assistant Examiner*—Laura L. Stockton
*Attorney, Agent, or Firm*—Frank S. Ungemach

[57] ABSTRACT

Sulfonylalkanoylamino hydroxyethylamino sulfamic acid compounds which are effective as retroviral protease inhibitors, and in particular as inhibitors of HIV protease.

94 Claims, No Drawings

SULFONYLALKANOYLAMINO HYDROXYETHYLAMINO SULFAMIC ACIDS USEFUL AS RETROVIRAL PROTEASE INHIBITORS

This application is a 371 PCT/US 93/10461 filed Oct. 29, 1993.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to sulfamic acid-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit vital replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors, "Science, 248, 358 (1990); and Erickson et al, "Design Activity, and 2.8 Å Crystal Structure of a $C_2$ Symmetric Inhibitor Complexed to HIV-1 Protease," Science, 249, 527 (1990).

Several classes of compounds are known to be useful as inhibitors of the proteolytic enzyme renin. See, for example, U.S. Pat. No. 4,599,198; U.K. 2,184,730; G.B. 2,209,752; EP 0 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. G.B. 2,200,115 also discloses sulfamic acid-containing hydroxyethylamine renin inhibitors, and EP 0264 795 discloses certain sulfamic acid-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as sulfonylalkanoylaminohydroxyethylamino sulfamic acid-containing inhibitor compounds.

DETAILED DESCRIPTION OF THE INVENTION

In accordance with the present invention, there is provided a retroviral protease inhibiting compound of the formula:

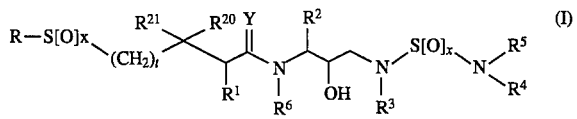

or a pharmaceutically acceptable salt, prodrug or ester thereof wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkyl, aminoalkylcarbonylalkyl, alkylcarbonylalkyl, aryloxyalkylcarbonyl, and aralkoxycarbonylalkyl radicals, aminoalkyl, and mono- and disubstituted aminoalkyl, mono- and disubstituted aminocarbonylalkyl and mono- and disubstituted aminoalkanoylalkyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or wherein said aminoalkyl, aminocarbonylalkyl and aminoalkanoylalkyl radicals are disubstituted, said substituents along with the nitrogen atom to which they are attached form a heterocycloalkyl or heteroaryl radical;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials, $-NO_2$, $-CN$, $-CF_3$, $-OR^9$ and $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ and $R^5$ independently represent hydrogen and radicals as defined by $R^3$ or together with a nitrogen atom to which they are bonded form a heterocycloalkyl or a heteroaryl radical;

$R^6$ represents hydrogen and alkyl radicals;

each x independently represents 1 or 2;

t represents either 0, 1, or 2; and

Y represents O, S and $NR^{15}$ wherein $R^{15}$ represents hydrogen and radicals as defined for $R^3$.

A family of compounds of particular interest within Formula I are compounds embraced by Formula II:

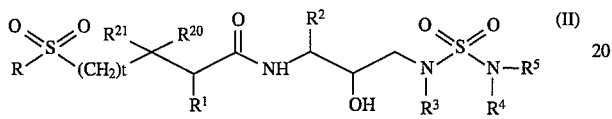

wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkyl, aralkoxyalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials, $-NO_2$, $-C\equiv N$, $CF_3$, $-OR^9$, $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ and $R^5$ independently represent hydrogen and radicals as defined by $R^3$, or together with the nitrogen atom to which they are bonded represent heterocycloalkyl and heteroaryl radicals; and t represents 0 or 1.

A more preferred family of compounds within Formula II consists of compounds wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen $CH_2C(O)NHCH_3$, $C(CH_3)_2(SCH_3)$, $C(CH_3)_2(S[O]CH_3)$, $C(CH_3)_2(S[O]_2CH_3)$, alkyl, alkenyl, alkynyl and cycloalkyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula $-OR^9$ and $-SR^9$ wherein $R^9$ represents alkyl radicals; and $R^3$ represents alkyl, haloalkyl, alkenyl, hydroxyalkyl, thioalkyl, alkoxyalkyl, alkylthioalkyl, cycloalkyl, cycloalkylalkyl, heterocycloalkyl, heterocycloalkylalkyl, aryl, aralkyl, heteroaryl and heteroaralkyl radicals;

$R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals, or $R^4$ and $R^5$ together with the nitrogen atom to which they are bonded from a heterocycloalkyl or heteroaryl radical; and t represents 0 or 1.

Of highest interest are compounds within Formula II wherein

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonyl and aralkoxycarbonylalkyl radicals;

$R^1$, $R^{20}$ and $R^{21}$ independently represent hydrogen $CH_2C(O)NHCH_3$, $C(CH_3)_2(SCH_3)$, $C(CH_3)_2(S[O]CH_3)$, $C(CH_3)_2(S[O]_2CH_3)$, methyl, propargyl, t-butyl, isopropyl and sec-butyl radicals, and amino acid side chains selected from the group consisting of asparagine, valine, S-methyl cysteine, methionine, allo-iso-leucine, iso-leucine, and beta-cyano alanine side chains;

$R^2$ represents $CH_3SCH_2CH_2-$, iso-butyl, n-butyl, benzyl, 4-fluorobenzyl, 2-naphthylmethyl and cyclohexylmethyl radicals;

$R^3$ represents propyl, isoamyl, n-butyl, isobutyl, cyclohexyl, cyclohexylmethyl, benzyl and pyridylmethyl radicals;

$R^4$ and propyl independently represent hydrogen and methyl, cyclohexyl, ethyl, i-propyl, n-butyl, t-butyl, 1,1-dimethylpropyl, and phenyl radicals, or together with the nitrogen atom to which they are bonded form a pyrrolidinyl, piperidinyl, morpholinyl, piperazinyl or N'-alkylpiperazinyl radical; and t is 0.

Another family of compounds of particular interest within Formula I are compounds embraced by Formula III:

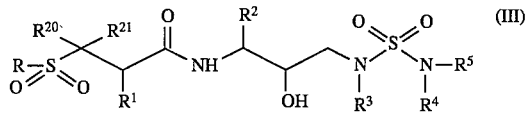

wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C\equiv N$, $CF_3$, $-OR^9$, $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof; and $R^4$ and $R^5$ independently represent hydrogen and radicals as defined for $R^3$ or together with a nitrogen atom to which they are bonded form a heterocycloalkyl or a heteroaryl radical.

A more preferred family of compounds within Formula III consists of compounds wherein R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, alkyl and alkenyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula $-OR^9$ and $-SR^9$ wherein $R^9$ represents hydrogen and alkyl radicals;

$R^3$ represents alkyl, haloalkyl, hydroxyalkyl, alkenyl, alkoxyalkyl, thioalkyl, alkylthioalkyl, cycloalkyl, cycloalkylalkyl, heterocycloalkyl, heterocycloalkylalkyl, aryl, aralkyl, heteroaryl and heteroaralkyl radicals; and $R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals, or $R^4$ and $R^5$ together with the nitrogen atom to which they are bonded from a heterocycloalkyl or heteroaryl radical.

Of highest interest are compounds within Formula III wherein

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, methyl, ethyl, propargyl, t-butyl, isopropyl and sec-butyl radicals, and amino acid side chains selected from the group consisting of asparagine, valine, S-methyl cysteine, methionine, allo-iso-leucine, iso-leucine, threonine, serine, aspartic acid, beta-cyano alanine, and allo-threonine side chains;

$R^2$ represents $CH_3SCH_2CH_2-$, iso-butyl, n-butyl, benzyl, 4-fluorobenzyl, 2-naphthylmethyl and cyclohexylmethyl radicals;

$R^3$ represents propyl, isobutyl, isoamyl, n-butyl, cyclohexyl, cyclohexylmethyl, benzyl and pyridylmethyl radicals; and $R^4$ and $R^5$ independently represent hydrogen and methyl, ethyl, propyl, i-propyl, n-butyl, t-butyl, 1,1-dimethylpropyl, cyclohexyl and phenyl radicals, or $R^4$ and $R^5$ together with the nitrogen atom to which they are bonded form a pyrrolidinyl, piperidinyl, morpholinyl, piperazinyl or N'-alkylpiperazinyl radical.

Another family of compounds of particular interest within Formula I are compounds embraced by Formula IV:

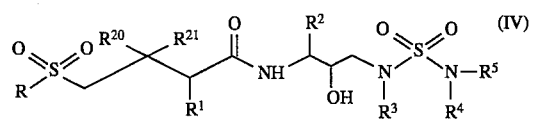

wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radials, $-NO_2$, $-C\equiv N$, $CF_3$, $-OR^9$ and $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof; and $R^4$ and $R^5$ independently represent hydrogen and radicals as defined by $R^3$, or together with the nitrogen atom to which they are bonded represent heterocycloalkyl and heteroaryl radicals.

A more preferred family of compounds within Formula IV consists of compounds wherein R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen and alkyl radicals having from 1 to about 4 carbon atoms, alkenyl, alkynyl, aralkyl radicals, and radicals selected from -$CH_2SO_2NH_2$, -$CO_2CH_3$, -$CONHCH_3$, -$CON(CH_3)_2$, -$CH_2C(O)NHCH_3$, -$CH_2C(O)N(CH_3)_2$, $CONH_2$, -$C(CH_3)_2(SCH_3)$ -$C(CH_3)_2(S[O]CH_3)$ and -$C(CH_3)_2(S[O]_2CH_3)$.

$R^2$ represents alkyl, cycloalkylalkyl and aralkyl radicals, which radicals are optionally substituted with halogen radicals and radicals represented by the formula -$OR^9$ and -$SR^9$ wherein $R^9$ represents hydrogen and alkyl radicals; and $R^3$ represents alkyl, haloalkyl, hydroxyalkyl, alkenyl, alkoxyalkyl, alkylthioalkyl, cycloalkyl, cycloalkylalkyl, heterocycloalkyl, heterocycloalkylalkyl, aryl, aralkyl, heteroaryl and heteroaralkyl radicals; and $R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals, or $R^4$ and $R^5$ together with the nitrogen atom to which they are bonded from a heterocycloalkyl or heteroaryl radical.

Of highest interest are compounds of Formula IV wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, methyl, ethyl, benzyl, phenylpropyl, -$C(O)NH_2$ and propargyl radicals;

$R^2$ represents $CH_3SCH_2CH_2$-, iso-butyl, n-butyl, benzyl, 4-fluorobenzyl, 2-naphthylmethyl and cyclohexylmethyl radicals;

$R^3$ represents propyl, isobutyl, isoamyl, n-butyl, cyclohexylmethyl, benzyl and pyridylmethyl radicals; and $R^4$ and $R^5$ independently represent hydrogen and methyl, ethyl, i-propyl, n-butyl, t-butyl, 1,1-dimethylpropyl and phenyl radicals, or together with the nitrogen atom to which they are bonded form a pyrrolidinyl, piperidinyl, morpholinyl, piperazinyl or N'-alkylpiperazinyl radical.

As utilized herein, the term "alkyl", alone or in combination, means a straight-chain or branched-chain alkyl radical containing from 1 to about 10, preferably from 1 to 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to 8 carbon atoms. Examples of suitable alkenyl radicals include ethenyl, propenyl, 1,4-butadienyl, 12-octadecene and the like. The term "alkynyl", alone or in combination, means a straight-chain hydrocarbon radical having one or more triple bonds and containing from 2 to about 10 carbon atoms, preferably from 2 to 8 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms and is cyclic. The term "cycloalkylalkyl" means an alkyl radical as defined above which is substituted by a cycloalkyl radical containing from about 3 to about 8, preferably from 3 to 6 carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro, cyano, haloalkyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula -C(O)-O-aralkyl in which the term "aralkyl" has the significance given above. An example of an aralkoxycarbonyl radical is benzyloxycarbonyl. The term "aryloxy" means a radical of the formula aryl-O- in which the term aryl has the significance given above. The term "alkanoyl", alone or in combination, means an acyl radical derived from an alkanecarboxylic acid wherein alkane means a radical as defined above for alkyl. Examples of alkanoyl radicals include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6- (benzyloxycarbonyl) -2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., -NH-) by alkyl, aralkoxycarbonyl, alkanoyl, phenyl or phenylalkyl or on a tertiary nitrogen atom (i.e. =N-) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Such heterocyclyl and heteroaryl radicals have from four to about 12 ring members, preferably from 4 to 10 ring members. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl 1,2,3,4-tetrahydro-1-oxo-isoquinolinyl, etc.), quinoxalinyl, β-carbolinyl, 2-benzofurancarbonyl, 1-,2-,4- or 5-benzimidazolyl, and the like. The term "cycloalkylalkoxycarbonyl" means an acyl group derived from a cycloalkylalkoxycarboxylic acid of the formula cycloalkylalkyl-O-COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O-COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O-COOH wherein heterocyclyl has the significance given above. The term "heteroaryloxycarbonyl" means an acyl radical derived from a carboxylic acid represented by heteroaryl-O-COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R), which is the preferred stereochemistry for the compounds of the present invention. However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedure. This procedure is schematically shown in the following Schemes I and II:

SCHEME I

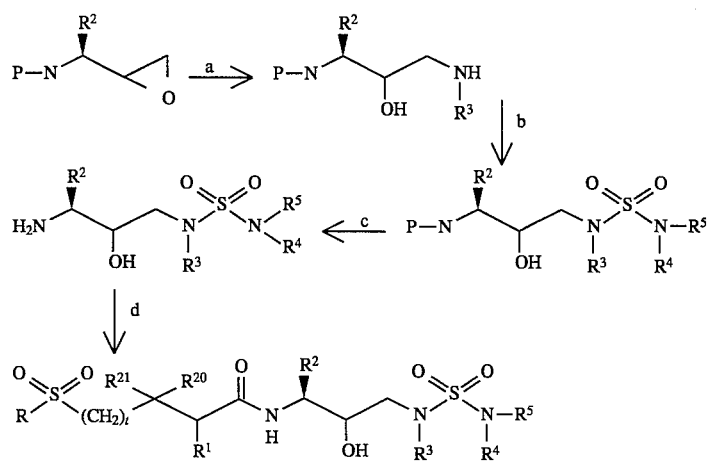

a) amine b) sulfamoyl chloride $R^4R^5NSO_2Cl$ (or anhydride)+acid scavenger d) coupling.

SCHEME II

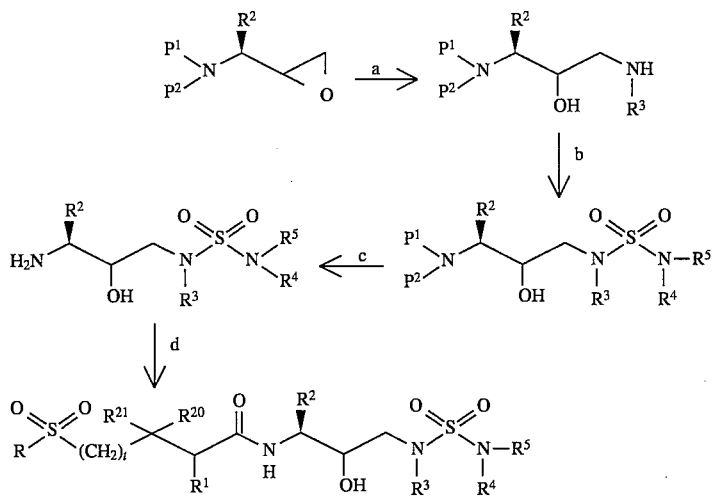

a) amine b) sulfamoyl chloride R⁴R⁵NSO₂Cl (or anhydride)+acid scavenger d) coupling.

An N-protected chloroketone derivative of an amine acid having the formula:

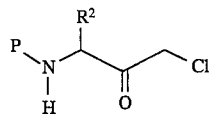

wherein P represents an amine protecting group, and $R^2$ is as defined above, is reduced to the corresponding alcohol utilizing an appropriate reducing agent. Suitable amine protecting groups are well known in the art and include carbobenzoxy, t-butoxycarbonyl, and the like. A preferred amine protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be utilized directly, as described below, or, preferably, is then reacted, preferably at room temperature, with a suitable base in a suitable solvent system to produce an N-protected amino epoxide of the formula:

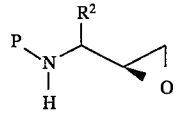

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

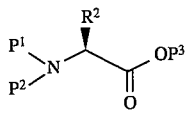

wherein $P^1$ and $P^2$ independently represent hydrogen, benzyl and amino-protecting groups (as defined above), provided that $P^1$ and $P^2$ are not both hydrogen; $P^3$ represents carboxyl-protecting group, e.g., methyl, ethyl, benzyl, tertiary-butyl and the like; and $R^2$ is as defined above.

The amino-protected L-amino acid ester is then reduced, to the corresponding alcohol. For example, the amino-protected L-amino acid ester can be reduced with diisobutylaluminum hydride at −78° C. in a suitable solvent such as toluene. The resulting alcohol is then converted, for example, by way of a Swern oxidation, to the corresponding aldehyde of the formula:

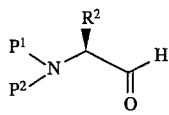

wherein $P^1$, $P^2$ and $R^2$ are as defined above. Thus, a dichloromethane solution of the alcohol is added to a cooled (−75° to −68° C.) solution of oxalyl chloride in dichloromethane and DMSO in dichloromethane and stirred for 35 minutes.

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

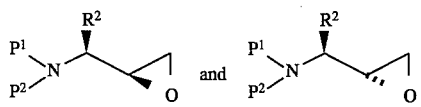

The diastereomers can be separated e.g., by chromatography, or, alternatively, once reacted in subsequent steps the diastereomeric products can be separated. For compounds having the (S) stereochemistry, a D-amine acid can be utilized in place of the L-amine acid.

The amino epoxide is then reacted, in a suitable solvent system, with an equal amount, or preferably an excess of, a desired amine of the formula:

wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) can be represented by the formulas:

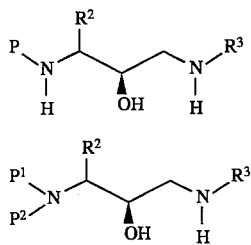

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with a sulfamoyl halide, e.g. sulfamoyl chloride ($R^4R^5NSO_2Cl$ or $R^4HNSO_2Cl$) or sulfamoyl anhydride in the presence of an acid scavenger. Suitable solvents in which the reaction can be conducted include methylene chloride, tetrahydrofuran and the like. Suitable acid scavengers include triethylamine, pyridine and the like. The resulting sulfamic acid derivative can be represented, depending on the epoxide utilized, by the formulas;

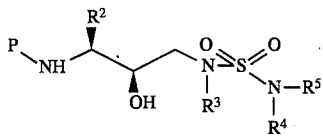

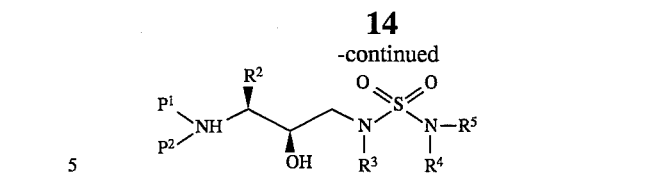

wherein P, $P^1$, $P^2$, $R^2$, $R^3$, $R^4$ and $R^5$ are as defined above. These intermediates are useful for preparing inhibitor compounds of the present invention and are also active inhibitors of retroviral proteases.

The sulfamoyl halides of the formula $R^4NHSO_2X$ can be prepared by the reaction of a suitable isocyanate of the formula $R^4NCO$ with fuming sulfuric acid to produce the corresponding sulfamate which is then converted to the halide by well known procedures, such as by treating the sulfamate with $PCl_5$. Alternatively, the isocyanate can be treated with chlorosulfonic acid to produce the corresponding sulfamoyl chloride directly.

The sulfamoyl halides of the formula $R^4R^5NSO_2Cl$ can be prepared by reacting an amine of the formula $R^4R^5NH$, preferably as a salt such as the hydrochloride, with sulfuryl chloride in a suitable solvent such as acetonitrile. The reaction mixture is gradually warmed to reflux temperature and maintained at the reflux temperature until the reaction is complete. Alternatively, sulfamoyl halides of the formula $R^4R^5NSO_2Cl$ can be prepared by reacting an amine of the fomula $R^4R^5NH$ with sulfuryl chloride in boiling MeCN as disclosed in Matier et al., *J. Med. Chem.*, 15, No. 5, p.538 (1972).

Following preparation of the sulfamic acid derivative, the amino protecting group P or the $P^1$ and $P^2$ amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Where the protecting group is a benzyl radical, it can be removed by hydrogenolysis. Following neutralization of the salt, the amine is then reacted with a sulfone of the formula

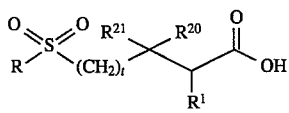

wherein R, $R^1$, $R^{20}$, $R^{21}$ and t are as defined above. The sulfone is prepared according to the following procedure to produce the antiviral compounds of the present invention having the formula:

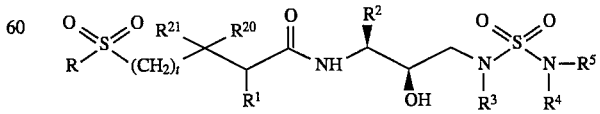

wherein R, $R^1$, $R^2$, $R^3$, $R^4$, $R^5$, $R^{20}$, $R^{21}$ and t are as defined above. The sulfone is prepared according to the following procedure.

A mercaptan of the formula RSH is reacted with a substituted methacrylate of the formula:

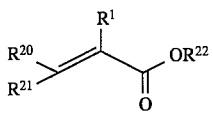

by way of a Michael Addition. The Michael Addition is conducted in a suitable solvent and in the presence of a suitable base, to produce the corresponding thiol derivative represented by the formula:

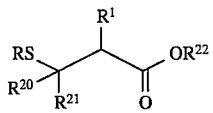

wherein R and $R^1$ represent radicals defined above; $R^{20}$ and $R^{21}$ represent hydrogen and radicals as defined for $R^1$; and $R^{22}$ represents a carboxyl protecting group such as methyl, ethyl, benzyl, t-butyl or the like. Suitable solvents in which the Michael Addition can be conducted include protic, non-protic and dipolar aprotic organic solvents, e.g., alcohols such as, for example, methanol, ethanol, butanol and the like, as well as ethers, e.g., THF, and acetonitrile, DMF, DMSO, and the like, including mixtures thereof. Suitable bases include Group I metal alkoxides such as, for example sodium methoxide, sodium ethoxide, sodium butoxide and the like as well as Group I metal hydrides, such as sodium hydride, including mixtures thereof.

The thiol derivative is converted into the corresponding sulfone or sulfoxide of the formula:

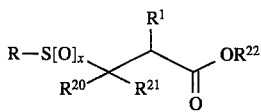

by oxidizing the thiol derivative with a suitable oxidation agent in a suitable solvent. Suitable oxidation agents include, for example, hydrogen peroxide, sodium metaperborate, oxone (potassium peroxy monosulfate), metachloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The sulfone is then converted to the corresponding free acid of the formula:

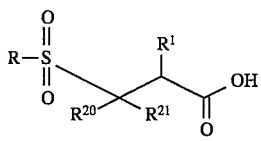

One method involves utilizing a suitable base, e.g., lithium hydroxide, sodium hydroxide, and the like, including mixtures thereof, in a suitable solvent, such as, for example, THF, water, acetonitrile, DMF, DMSO, methylene chloride and the like, including mixtures thereof. Other methods which can be used for deprotection depend on the nature of $R^{22}$. For example, when $R^{22}$ is a tertiary-butyl group, one can use a strong acid such as hydrochloric acid or trifluoroacetic acid. When $R^{22}$ is a benzyl group, it can be removed via hydrogenolysis.

The free acid is then coupled, utilizing procedures well known in the art, to the sulfamate derivative, or analog thereof, of an amino alcohol which is described above. The resulting product is a compound represented by Formula I.

Alternatively, one can couple the sulfamate isostere to the commercially available acid,

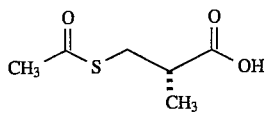

remove the thioacetyl group with a suitable base, such as hydroxide, or an amine, such as ammonia, and then react the resulting thiol with an alkylating agent, such as an alkyl halide, tosylate or mesylate to afford compounds at the following structure:

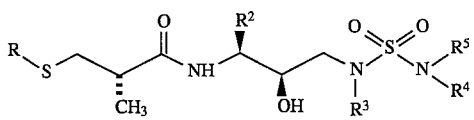

The sulfur can then be oxidized to the corresponding sulfone or sulfoxide using suitable oxidizing agents, as described above, to afford the desired compounds of the following structure:

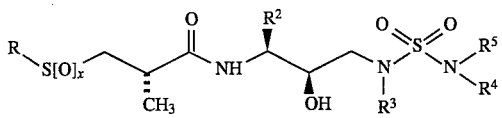

Alternatively, to prepare compounds of Formula I, a substituted methacrylate of the formula:

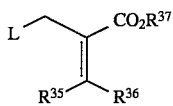

wherein L represents a leaving group as previously defined, $R^{35}$ and $R^{36}$ represent hydrogen and radicals as defined for $R^1$; and $R^{37}$ represents alkyl, aralkyl, cycloalkyl and cycloalkylalkyl radicals, is reacted with a suitable sulfonating agent, such as, for example, a sulfinic acid represented by the formula $RSO_2M$, wherein R represents radicals as defined above and M represents a metal adapted to form a salt of the acid, e.g., sodium, to produce the corresponding sulfone represented by the formula:

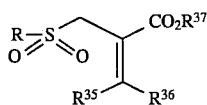

wherein R, $R^{35}$, $R^{36}$ and $R^{37}$ are as defined above. The sulfone is then hydrolyzed in the presence of a suitable base, such as lithium hydroxide, sodium hydroxide and the like, to the compound represented by the formula:

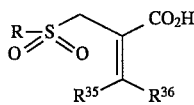

wherein R, $R^{35}$ and $R^{36}$ represent radicals as defined above. The resulting compound is then asymmetrically hydrogenated utilizing an asymmetric hydrogenation catalyst such as, for example, a ruthenium-BINAP complex, to produce the reduced product, substantially enriched in the more active isomer, represented by the formula:

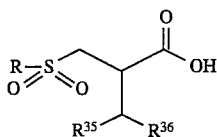

wherein R, $R^{35}$ and $R^{36}$ represent radicals as defined above. Where the more active isomer has the R-stereochemistry, a Ru(R-BINAP) asymmetric hydrogenation catalyst can be utilized. Conversely, where the more active isomer has the S-sterochemistry, a Ru(S-BINAP) catalyst can be utilized. Where both isomers are active, or where it is desired to have a mixture of the two diastereomers, a hydrogenation catalyst such as platinum, or palladium, on carbon can be utilized to reduce the above compound. The reduced compound is then coupled to the sulfamate isostere, as described above, to produce compounds of Formula II.

Alternatively, an acid or a derivative of an acid properly substituted with a leaving group (discussed above) can be treated with a mercaptan and a base (see above) to provide an organic sulfide. Acid derivatives are defined above. The resulting sulfide can be oxidized to the corresponding sulfoxide or sulfone by methods previously discussed.

A preferred method to prepare 2(S)-methyl-3-(methylsulfonyl)propionic acid is as follows. Beginning with the commercially available compounds of the following structure;

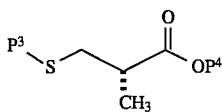

Where $P^3$ is a protecting group for sulfur, preferably a benzoyl or acetyl, and $P^4$ is either hydrogen or a carboxylic acid protecting group such as methyl, ethyl, tertiary-butyl, benzyl and the like. Preferably, $P^4$ is tertiary-butyl. The sulfur protecting group $P^3$ can be selectively removed using methods known to those skilled in the art. For example, where P3 is either benzoyl or acetyl, it can be removed by treatment with an inorganic base or an amine, preferably ammonia, in an appropriate solvent such as methanol, ethanol, isopropanol, toluene or tetrahydrofuran. The preferred solvent is methanol. This provides a compound of the following structure;

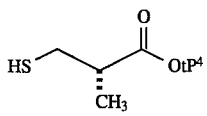

which can be alkylated on the sulfur with a compound of the structure

RX

Where R is as defined above, and X is an appropriate leaving group, such as a halide (chloride, bromide, iodide), mesylate, tosylate or triflate. The reaction is performed in the presence of a suitable base, such as triethylamine, diisopropylethylamine, 1,8-diazabicyclo[5.4.0] undec-7-ene (DBu) and the like, in a suitable solvent such as toluene, tetrahydrofuran, or methylene chloride. The preferred base is DBU and the preferred solvent is toluene. Where R is a methyl group, RX can be methyl chloride, methyl bromide, methyl iodide, or dimethyl sulfate. Preferably RX is methyl iodide. The product of the reaction is a compound of the structure;

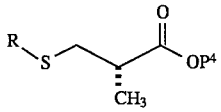

The sulfur can then be oxidized to either the sulfoxide or sulfone using methods known to those skilled in the art. Suitable oxidizing agents are meta-chloroperbenzoic acid, hydrogen peroxide, sodium perborate and the like. Appropriate solvents are methylene chloride, toluene, acetic acid, propionic acid and the like. The preferred method is using hydrogen peroxide or sodium perborate in acetic acid. The sulfone produce has the structure;

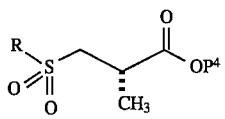

The carboxylic acid protecting group $P^4$ can then be removed using methods well known to those in the art. For example, when $P^4$ is a tertiary-butyl group, it can be removed by treatment with an acid, such as hydrochloric acid or trifluoracetic acid. The preferred method is using 4N hydrochloric acid in dioxane. This provides the desired final compound of the structure;

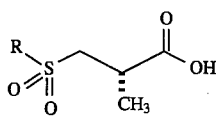

Alternatively, the protected amino alcohol from the epoxide opening can be further protected at the newly introduced amino group with a protecting group P' which is not removed when the first protecting P is removed. One skilled in the art can choose appropriate combinations of P and P'. One suitable choice is when P is Cbz and P' is Boc. The resulting compound represented by the formula:

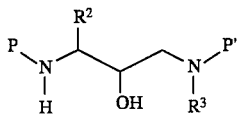

can be carried through the remainder of the synthesis to provide a compound of the formula:

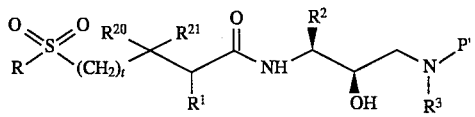

and the new protecting group P' is selectively removed, and following deprotection, the resulting amine reacted to form the sulfamic acid derivative as described above. This selective deprotection and conversion to the sulfamic acid can be accomplished at either the end of the synthesis or at any appropriate intermediate step if desired.

It is contemplated that for preparing compounds of the Formulas having $R^6$, the compounds can be prepared following the procedure set forth above and, prior to coupling the sulfamate derivative or analog thereof, e.g. coupling to the amino acid PNH(CH₂)ₓCH(R¹)COOH, carried through a procedure referred to in the art as reductive amination. Thus, a sodium cyanoborohydride and an appropriate aldehyde or ketone can be reacted with the sulfamate derivative compound or appropriate analog at room temperature in order to reductively aminate any of the compounds of Formulas I–IV. It is also contemplated that where R³ of the amino alcohol intermediate is hydrogen, the inhibitor compounds of the present invention wherein R³ is alkyl, or other substituents wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties, such as tautomers thereof as well as compounds, wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples 1 through 9 illustrate preparation of intermediates. These intermediates are useful in preparing the inhibitor compounds of the present invention as illustrated below.

EXAMPLE 1

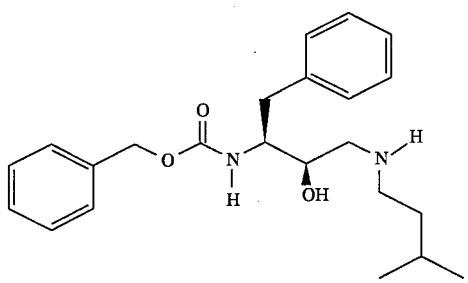

Preparation of N[3 (S)-benzyloxycarbonylamino-2(R)-hydroxy-4-phenylbutyl]-N-isoamylamine Part A To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li⁺=340.

Part B

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102°–103° C. and MH⁺ 298.

Part C

A solution of N-benzyloxycarbonyl 3(S)-amino-1,2-(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0°–109.5° C., MH⁺ m/z=371.

EXAMPLE 2

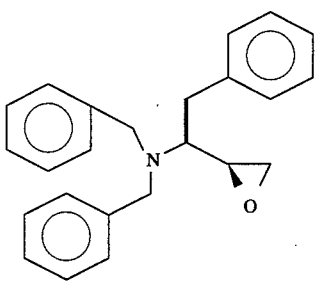

Preparation of
N,N-dibenzyl-3(S)-amino-1,2-(S)-epoxy-4-phenylbutane

Step A

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to −55° C. A 1.5M solution of DIBAL-H in toluene (443.9 ml, 0.666 mol) is then added at a rate to maintain the temperature between −55° to −50° C. (addition time—1 hour). The mixture is stirred for 20 minutes at −55° C. The reaction is quenched at −55° C. by the slow addition of methanol (37 ml). The cold solution is then poured into cold (5° C.) 1.5N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of matrial can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to −74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min. followed by addition of a solution of the alcohol (0.074 mol) in 100 ml of dichloromethane (addition time ~20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to −78° C. A 1.6M solution of n-butyllithium in hexane (25 ml, 0.040 mol) is then added at a rate to maintain the temperature at −75° C. (addition time—15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a b rown oil (27.4 g). The product could be used in the next step without purification. The desired diastereomer can be purified by recrystallization at a subsequent step.

Alternately, the product could be purified by chromatography.

EXAMPLE 3

Preparation of
N[3(S)-benzyloxycarbonylamino-2(R)-hydroxy-4-phenyl]N-isobutylamine A solution of N-benzyloxycarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl]N-isobutylamine, mp 108.0°–109.5° C., MH+ m/z=371.

EXAMPLE 4

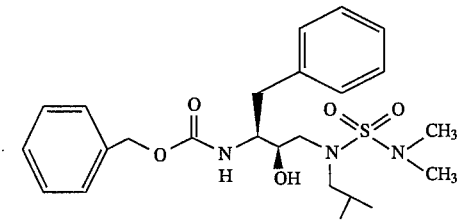

Preparation of phenylmethyl [2R-hydroxy-3-[[(dimethylamino)sulfonyl](2-methylpropyl)amino]-1S-(phenylmethyl)propyl]carbamate Part A The procedure described in Example 3 was used to prepare N[3(S)-benzyloxycarbonylamino-2(R)-hydroxy-4-phenylbutyl]-N-isobutylamine.

Part B

The product from Part A (740 mg, 2.0 mmol) and diisopropylethylamine (382 uL, 2.2 mmol) were dissolved in dichloromethane (1.5 mL) at room temperature. To this was added dimethylsulfamoyl chloride (354 uL, 3.3 mmol). The reaction was stirred for 24 hours. The reaction mixture was chromatographed on silica gel (50 gm) using 1% ethanol in chloroform. The product fractions were pooled and concentrated to an oil. Anal. Calcd for $C_{24}H_{35}N_3O_5S$: C, 60.35; H, 7.39; N, 8.80. Found: C, 60.18; H, 7.40; N, 8.55.

EXAMPLE 5

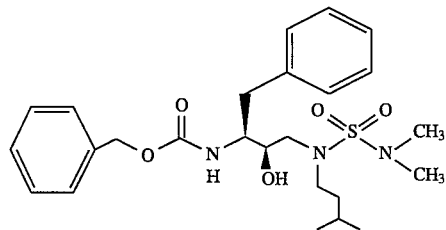

Preparation of phenylmethyl[2R-hydroxy-3-[[(dimethylamino)sulfonyl](3-methylbutyl)amino]-1S-(phenylmethyl)propyl]carbamate Part A The procedure described in Example 1 was used to prepare N[3(S)-benzyloxycarbonylamino-2(R)-hydroxy-4-phenylbutyl]-N-[(3-methylbutyl)]amine.

Part B

The product from Part A (192 mg, 0.5 mmol) and diisopropylethylamine (96 uL, 0.55 mmol) were dissolved in dichloromethane (10 mL) at room temperature. To this was added dimethylsulfamoyl chloride (59 uL, 0.55 mmol). The reaction was stirred for 120 hours, then concentrated on a rotary evaporator. The residue was chromatographed on silica gel (50 gm) using 2% methanol in dichloromethane. The product fractions were pooled and concentrated to an oil which solidified on standing. Anal. Calcd for $C_{25}H_{37}N_3O_5S$.

0.9 $H_2O$: C, 59.13; H, 7.64; N, 8.27; S, 6.31. Found: C, 58.81; H, 7.38; N, 8.62; S, 6.70.

EXAMPLE 6

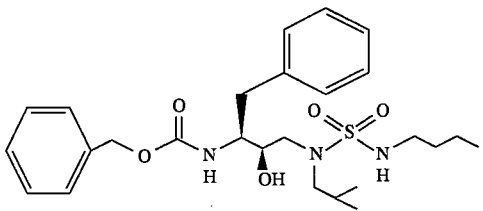

Preparation of phenylmethyl [3-[[(butylamino)sulfonyl](2-methylpropyl)amino]-2R-hydroxy-1S-(phenylmethyl)propyl]carbamate Part A The procedure described in Example 3 was used to prepare N[3(S)-benzyloxycarbonylamino-2(R)-hydroxy-4-phenylbutyl]-N-isobutylamine.

Part B

To a stirred solution of 3.88 gm (2 mL) of 30% fuming sulfuric acid in nitromethane (10 mL) was added dropwise n-butylisocyanate (3.83 mL, 34 mmoles) at 0 C. After the addition was completed, the suspension was heated in an oil bath at 120 C. for 30 min. The reaction was cooled and filtered. The collected sulfamic acid crystals were air dried, wt. 4.73 gm (91%).

Part C

A suspension of n-butyl sulfamic acid 1.92 gm, 12.53 mmoles) and phosphorus pentachloride (2.61 gm, 12.53 mmoles) in benzene (20 mL) was warmed gently to initiate gas evolution. The reaction mixture was stirred at room temperature for 0.5 h., during which time a cloudy solution resulted. The cloudy solution was heated to reflux for 0.5 h., then was concentrated. The produce n-outyl sulfamoyl chloride was isolated by vacuum distillation (120 C., 300 millitorr), 730 mg (liq.) (34%).

Part D

The amino alcohol from Part A (370 mg, 1 mole) was dissolved in 3 mL of dichloromethane and treated with diisopropylethylamine (278 uL, 2 moles), followed by chlorotrimethylsilane (126 uL, 1 mmole). The reaction mixture was stirred an r.t. for 1 h. n-Butyl sulfamoyl chloride from Part C (171 mg, 1 mole) was added and the mixture was stirred at r.t. overnight. After removal of dichloromethane the oily residue was taken up in ethyl acetate and washed successively with 5% citric acid, saturated sodium bicarbonate, brine, dried over sodium sulfate and the solvent was evaporated to give 512 mg of product (oil).

The oily produce (510 mg) was dissolved in dichloromethane (3 mL) and was treated with 2 mL of 4N HCl in dioxane. After 15 min. methanol (5 mL) was added and the solution was stirred for an additional 15 min. Solvent and excess reagent were evaporated. The product was isolated by silica gel chromatography to give 357 mg of phenylmethyl [3-[[(butylamino)sulfonyl](2-methylpropyl)amino]-2R-hydroxy-1S-(phenylmethyl)propyl]carbamate. Anal. Calcd for $C_{26}H_{39}N_3O_5S$: C, 61.76; H,7.77; N,8.31. Found: C, 61.89; H,7.66; N, 8.18.

EXAMPLE 7

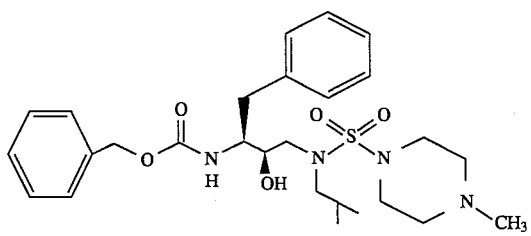

Preparation of phenylmethyl
[2R-hydroxy-3-[[(4-methyl-1-piperazinyl)sulfonyl)]
(2-methylpropyl)amino]-1S-(phenylmethyl)propyl]
carbamate Part A 1-methylpiperazine hydrochloride (3.46 gm, 20 mmoles) was added in portions within 15 min. to a stirred solution of sulfuryl chloride (8.99 gm, 67 mmoles) in acetonitrile(40 mL). The suspension was gradually warmed to reflux and maintained at reflux temperature overnight. A brown solution was obtained. After cooling to r.t., the crystals were collected by filtration, wt. 2.3 gm. A sample of 4-methyl-1-piperazine sulfamoyl chloride.HCl was recrystallized from methanol. Anal. Calcd. for $C_5H_{12}N_2O_2Cl_2S$: C, 25.54; H, 5.14; N, 11.91; Cl, 30.16. Found: C, 25.54; H, 4.91; N, 11.91; Cl, 29.88.

Part B

N[3(S)-benzyloxycarbonylamino-2(R)-hydroxy-4-phenylbutyl]-N-isobutylamine (370 mg, 1.0 mmole), prepared according to the procedure in Example 3 was mixed with DIEA (280 uL, 2.0 mmoles) and 4-methyl-1-piperazine sulfamoyl chloride.HCl (240 mg, 1.0 mmole) in 6 mL of dichloromethane. The reaction mixture was stirred for 5 days. After filtration, the filtrate was concentrated to an oil, which was taken up in ethyl acetate. The ethyl acetate solution was washed with sodium bicarbonate solution, brine and dried over sodium sulfate. After evaporation, phenylmethyl [2R-hydroxy-3-[[(4-methyl-1-piperazinyl)sulfonyl](2-methylpropyl)amino]-1S-(phenylmethyl)propyl] carbamate was obtained (412 mg).

EXAMPLE 8

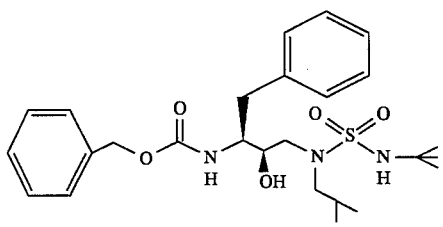

Preparation of phenylmethyl
[2R-hydroxy-3-[[(1,1-dimethyl)amino]sulfonyl]
(2-methylpropyl)amino]-1S-(phenylmethyl)propyl]
carbamate Part A A 25 mL two-necked RB flask, equipped with a reflux condenser and dropping funnel and under a nitrogen atmosphere, was charged with t-butanol (207 uL, 2.2 mmoles) and 5 mL of hexane. Chlorosulfonyl isocyanate (192 uL, 2.2 mmoles) in 3 mL of hexane was added dropwise. Upon warming a homogeneous solution was obtained. The solution was heated at gentle reflux for 45 min., then was cooled to r.t. Solvent was removed under a steady stream of nitrogen. The crude t-butyl sulfamoyl chloride (a liquid) was used without further purification.

Part B

N[3(S)-benzyloxycarbonylamino-2(R)-hydroxy-4-phenylbutyl]-N-isobutylamine (370 mg, 1.0 mmole), prepared according to the procedure in Example 3 was mixed with DIEA (139 uL, 1 mmole) in 5 mL of dichloromethane. Chlorotrimethylsilane (126 uL, 1 mmole) was added. After 1 h., additional DIEA (160 uL) was added, followed by a dichloromethane solution (5 mL) containing 1.1 mmole of t-butyl sulfamoyl chloride from Part A. The reaction mixture was stirred for 2 days. Solvent was removed under aspirator pressure. The oily residue was taken up in ethyl acetate and washed with 5% citric acid, saturated sodium bicarbonate, brine, dried over sodium sulfate and evaporated to an oily residue (380 mg).

The crude product was stirred in 4N HCl in dioxane (6 mL) for 15 min. After the addition of 4 mL of methanol to the reaction mixture, the solution was stirred for an additional 15 min, then concentrated to an oily residue. The product, phenylmethyl [2R-hydroxy-3-[[(1,1-dimethylethyl)amino]sulfonyl](2-methylpropyl)amino]-1S-(phenylmethyl)propyl] carbamate was obtained after silica gel chromatography (188 mg, 37%). MS $(MH)^+$=506.

Part C

The carbobenzyloxy protecting group of the product from Parg B was removed by hydrogenolysis. Thus 1.3 grams of the product of Part B in 50 mL of methanol was hydrogenated under 50 psig of hydrogen using 0.7 g of 10% palladium-on-carbon catalyst 18 hours. The catalyst was removed by filtration and the solvent removed in vacuo to afford 0.75 g of the free amine.

EXAMPLE 9

Phenylmethyl
[2R-hydroxy-3-[[(piperidyl)sulfonyl](2-methylpropyl)
amino]-1S-(phenylmethyl)propyl]carbamate Part A The product of Example 3 (750 mg, 2.02 mmol) and triethylamine (280 uL, 2.02 mmol) were dissolved in dichloromethane (8.0 mL) at room temperature. To this was added piperidinesulfamoyl chloride (371 mg, 2.02 mmol). The reaction was stirred for 72 hours and then concentrated. The residue was chromatographed on silica gel (50 gm) using 5% methanol in dichloromethane. The product fractions were pooled and concentrated to an oil, 945 mg. TLC (silica/5% MeOH in CH2Cl2) showed two spots. Rechromatographed. Anal. Calcd for $C_{27}H_{39}N_3O_5S$: C, 62.63; H, 7.51; N, 8.06. Found: C, 62.64; H, 7.59; N, 8.12.

Part B

The product of Part A (430 mg) was combined with 10% Pd/C in methanol (10 mL) and hydrogenated at 5 psi for 1.4 hours at room temperature. The catalyst was removed by filtration and the solvent evaporated to afford the product as an oil, 305 mg.

Part C

To a solution of Cbz-L-t-leucine (236 mg, 0.89 mmol) in DMF (2 mL) was added HOBt (115 mg, 0.85 mmol) and EDC (163 mg, 0.85 mmol). The reaction was stirred at room temperature for 1 hour and then a solution of the product from part B (305 mg, 0.79 mmol) in DMF (2 mL) was added. The reaction was stirred for 18 hours then concentrated. The residue was taken up in ethyl acetate and washed with 0.5% HCl solution, saturated aqueous NaHCO3, and saturated aqueous NaCl (50 mL each). The organic solution was dried (Na2SO4), filtered and concentrated to a foam, 410 mg. 1H NMR supports product.

Part D

The product of Part C (410 mg) was combined with 10% Pd/C in methanol (10 mL) and hydrogenated at 5 psi for 2.0 hours at room temperature. The catalyst was removed by filtration and the solvent evaporated to afford the product as an foam, 320 mg.

Part E

To a solution of the product of Part D (310 mg, 0.62 mmol) in dichloromethane (10 mL) was added diisopropylethylamine (130 uL, 0.75 mmol and chloroacetic anhydride (117 mg, 0.68 mmol) at 0 C. The reaction was allowed to warm to room temperature and stir one hour. The solvent was removed and the residue taken up in ethyl acetate (50 mL). The organic solution was washed with 5% citric acid, saturated NaHCO3, and saturated NaCl (50 mL each). The solution was dried (Na2SO4), filtered and concentrated to give a solid, 350 mg.

Part F

The product of Part E (350 mg, 0.61 mmol) was combined with 40% aqueous dimethylamine (380 uL, 3.05 mmol) in isopropanol (10 mL). The reaction was stirred for 18 hours then concentrated. The residue was taken up in ethyl acetate (50 mL) and washed with water, saturated NaHCO3, and saturated NaCl (50 mL each). The solution was dried (Na2SO4), filtered and concentrated to a solid. The solid was chromatographed on silica gel using 2% MeOH in dichloromethane. The product fractions were pooled and concentrated to give a white solid. Anal. Calcd for C29H51N5O5S. 0.25 H2O: C, 59.41; H, 8.77; N, 11.94. Found: C, 59.35; H, 8.78; N, 11.63.

EXAMPLE 10

Following the procedures of the previous Examples 1–9, the intermediate compounds set forth in Tables 1A, 1B and 1C were prepared.

TABLE 1A

| $R^3$ | $R^4$ | $R^5$ |
|---|---|---|
| isobutyl | $CH_3$ | $CH_3$ |
| isoamyl | $CH_3$ | $CH_3$ |
| isobutyl | $CH_2CH_2CH_2CH_3$ | H |
| isobutyl | $C(CH_3)_3$ | H |

TABLE 1B

| Entry | $R^4$ | $R^5$ |
|---|---|---|
| 1 | $CH_3$ | $CH_3$ |
| 2 | H | $CH_3$ |
| 3 | H | $(CH_2)_3CH_3$ |
| 4 | H | $CH(CH_3)_2$ |
| 5 | H | $C(CH_3)_3$ |
| 6 | H | $C_6H_{11}$ |
| 7 | H | $C_6H_5$ |
| 8 | pyrrolidine (N-) | |

TABLE 1C

| Entry | $R^3$ | $R^4$ | $R^5$ |
|---|---|---|---|
| A | isobutyl | methyl | H |
| B | p-fluorobenzyl | methyl | methyl |
| C | isobutyl | isopropyl | H |
| D | isobutyl | $NR^4R^5$ = | N-methylpiperazine |
| E | isobutyl | phenyl | H |
| F | isobutyl | $NR^4R^5$ = | pyrrolidine |
| G | isobutyl | $NR^4R^5$ = | piperidine |
| H | benzyl | t-butyl | H |
| I | cyclohexylmethyl | t-butyl | H |
| J | $C(CH_3)_2CO_2Me$ | isobutyl | H |
| K | cyclohexyl | t-butyl | H |
| L | isobutyl | $(CH_2)_2OCH_2C_6H_5$ | H |
| M | isobutyl | cyclohexyl | H |

The following Examples 11–14 illustrate preparation of sulfonyl alkanoyl compounds which can be coupled to the intermediate compounds of Examples 1–10 to produce inhibitor compounds of the present invention.

EXAMPLE 11

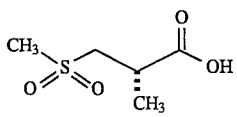

Preparation of
2(S)-methyl-3-(methylsulfonyl)propionic Acid.

To a solution of 10 g of D-(-)-S-benzoyl-b-mercaptio-isobutyric acid t-butyl ester in 20 mL of methanol was bubbled in gaseous ammonia at 0° C. The reaction was allowed to then warm to room temperature, stirred overnight and concentrated under reduced pressure. The resulting mixture of a solid (benzamide) and liquid was filtered to provide 5.21 g of a pale oil which then solidified. This was identified as 2(S)-methyl-3-mercaptopropionic acid t-butyl ester.

To a solution of 5.21 g of 2(S)-methyl-3-mercaptopropionic acid t-butyl ester in 75 mL of toluene at 0° C. was added 4.50 g of 1,8-diazabicyclo[5.40]undec-7-ene and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester.

To a solution of 2.82 g of 2(S)-methyl-3-(thiomethyl)propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid.

To 2.68 g of 2(S)-methyl-3-(methylsulfonyl)propionic acid t-butyl ester was added 20 mL of 4N hydrochloric acid/dioxane and the mixture stirred at room temperature for 19 hours. The solvent was removed under reduced pressure to afford 2.18 g of crude product, which was recrystallized from ethyl acetate/hexane to yield 1.44 g of 2(S)-methyl-3-(methylsulfonyl)propionic acid as white crystals.

EXAMPLE 12

Part A

A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 h and then concentrated in vacuo to give an oil that was taken up in ether and washed with 1N aqueous potassium hydrogen sulfate, saturated aqueous sodium chloride, dried over anhydrous magnesium sulfate, filtered and concentrated to give 16.83 g, 97.5% of methyl 2-(R,S)-methyl-4-thia-6-phenyl hexanoate as an oil. TLC on $SiO_2$ eluting with 20:1 hexane:ethyl acetate (v:v) $R_f$=0.41. Alternatively, one can use methyl 3-bromo-2-methyl propionate in place of methyl methacrylate.

Part B

A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 m. The solution was stirred at room temperature for 16 h and then filtered and the filterate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 m and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R,S)-methyl-3(β-phenethylsulfonyl)-propionic acid, mp 91°–93° C.

Part C

A solution of 2-(R,S)-methyl-3(β-phenethylsulfonyl)-propionic acid (166.1 mg, 0.65 mmol), N-hydroxybenzotriazole (HOBT) (146.9 mg, 0.97 mmol), and 1-(3-dimethylaminopropyl)-3-ethylcarbodiimide hydrochloride (EDC) (145.8 mg, 0.75 mmol) in 4 mL of anhydrous dimethylformamide (DMF) cooled to 0° C. and stirred under nitrogen for 0.5 h. This solution is then treated with a desired sulfonamide isostere and stirred at room temperature for 16 h. The solution is poured into 30 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated. Flash chromatography of the mixture on silica gel eluting with 1:1 hexane:ethyl acetate can be utilized and will afford the separated diastereomers.

EXAMPLE 13

Part A

A solution of methyl 2-(bromomethyl)-acrylate (26.4 g, 0.148 mol) in 100 mL of methanol was treated with sodium methanesulfinate (15.1 g, 0.148 mol) portion wise over 10 m at room temperature. The solution was then stirred at room temperature for a period of 1.25 h and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65–68 0° C.

Part B

A solution of methyl 2-(methylsulfonylmethyl) acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 m and then acidified to pH=1 with 1N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl) acrylic acid, mp 147–149 0° C.

Part C

A solution of 2-(methylsulfonylmethyl) acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 h and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid.

Part D

A solution of 2-(R,S)-methyl-3(methylsulfonyl) propionic acid (263.5 mg, 1.585 mmol), N-hydroxybenzotriazole (HOBT) (322.2 mg, 2.13 mmol), and 1-(3-dimethylaminopropyl)-3-ethylcarbodiimide hydrochloride (EDC) (339.1 mg, 1.74 mmol) in 4 mL of anhydrous dimethylformamide (DMF) is cooled to 0° C. and stirred under nitrogen for 0.5 h. This solution is then treated with a desired sulfonamide and stirred at room temperature for 16 h. The solution is poured into 60 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated to give the desired product.

EXAMPLE 14

Preparation of Sulfone Inhibitors From L-(+)-S-acetyl-β-mercaptoisobutyric Acid

Part A

A round-bottomed flask is charged with the desired sulfamic acid isostere (2.575 mmol), for example, the amine from Example 8, Part C, can be coupled to L-(+)-S-acetyl-β-mercapto butyric acid in the presence of 1-(3-dimethylaminopropyl)-3-ethylcarbodiimide hydrochloride (EDC) (339.1 mg, 1.74 mmol), in 10 mL of $CH_2Cl_2$ and is allowed to stir at room temperature for 16 h. The solution is concentrated in vacuo and the residue taken up in ethyl acetate, washed with 1N $KHSO_4$ sat. aq. $NaHCO_3$, brine, dried over anhydrous $MgSO_4$, filtered and concentrated to give an oil which can be purified by radial chromatography on $SiO_2$ eluting with ethyl acetate to give the pure product.

Part B

A solution of the product of Part A 0.85 mmol) in 10 mL of methanol is treated with anhydrous ammonia for ca. 1 m at 0° C. The solution is stirred at that temperature for 16 h and then concentrated in vacuo to give the desired product that can be used directly in the next step without further purification.

Part C

A solution of the product of Part B (0.841 mmol) in 10 mL of dry toluene under nitrogen is treated in rapid succession with 1,8-diazabicyclo[5.4.0]undec-7-ene, (DBU), (128.1 mg. 0.841 mmol) and iodomethane (119.0 mg, 0.841 mmol). After 0.5 h at room temperature the reaction is diluted with ethyl acetate washed with 1N $KHSO_4$, sat. aq. $NaHCO_3$, brine. After the solution is dried over anhydrous $MgSO_4$, filtered and concentrated in vacuo the desired product is obtained and can be used directly in the next step.

Part D

A solution of the product of Part C (0.73 mmol) and sodium perborate (500 mg, 3.25 mmol) in 30 mL of glacial acetic acid is warmed to 55° C. for 16 h. The solution is conentrated in vacuo and then the residue is taken up in ethyl acetate, washed with water, sat. aq. $NaHCO_3$, brine, dried over anhydrous $MgSO_4$, filtered and concentrated to give the desired product.

Representative sulfones prepared according to the above general procedures are shown in Table 2.

TABLE 2

| Entry | R |
|---|---|
| 1 | $CH_3-$ |
| 2 | $PhCH_2CH_2-$ |
| 3 | $Ph-$ |

General Procedure for Coupling Sulfonyl Alkanoyl Compounds to Sulfamic Acid Compounds A mixture of the sulfonyl alkanoyl compound (approximately 1 mmol), N-hydroxybenzotriazole (1.5 mmol), and 1-(3-dimethylaminopropyl)-3-ethylcarbodiimide hydrochloride (EDC) (1.2 mmol) is dissolved in a suitable solvent such as DMF and allowed to react for about 30 min. at 0° C. The sulfamic acid compounds, for example the amine from example 8, part c, (1.05 mmol) is dissolved in DMF, added to the above mixture and stirred at room temperature for a period of time sufficient for the reaction to take place. The solution is then poured into saturated aqueous $NaHCO_3$ and extracted with, for example, ethyl acetate. The extracts are washed, dried, filtered and concentrated. The resulting material is then crystallized from a suitable solvent or solvent mixture such as hexanes and ethyl acetate to produce the product, or alternatively purified by chromatography.

General Procedure for Preparation of Sulfamoyl Chlorides

A. To a solution of 547 mmol of sulfuryl chloride in 100 mL of anhydrous acetonitrile under a nitrogen atmosphere, was added 136 mmol of amine hydrochloride and the mixture heated to reflux for twenty-four to forty-eight hours. The solution was cooled and concentrated in vacuo to afford a semi-solid. Anhydrous diethyl ether was added, the solids removed by filtration are the filtrate concentrated to afford the crude sulfamoyl chloride. This can be used as is, or if desired, purified by either crystallization or distillation.

B. Preparation of Sulfamoyl Chlorides

Method A

An amino acid ester hydrochloride (1 mmol) is suspended in a suitable solvent such as hexane, dichloromethane, toluene and the like, but most preferable acetonitrile. To the well stirred mixture is added sulfuryl chloride (3 mmol) in a suitable solvent, or neat, dropwise over several minutes. The reaction is allowed to stir at zero to reflux temperatures, preferable at reflux, for 1 to 48 hours, preferably for 24 hours. The solvent is removed and the residue triturated with a suitable solvent, such as hexane, pentane, toluene, but most preferably diethyl ether. The solvent is decanted and concentrated. The product may then be utilized as such or purified by distillation or in the case of solids recrystallized from appropriate solvents.

Method B

An alpha-hydroxy ester (1 mmol) is dissolved in an appropriate solvent such as acetonitrile, dichloromethane, toluene and the like, but most preferable hexane. Chlorosulfonyl isocyanate (1 mmol) added neat or in a solvent, preferably in hexane, is added dropwise. The reaction is stirred from zero to reflux, preferably at reflux, for 5 minutes to several hours, preferably for 1 hour. The solvent is then removed and the residue used as such, or taken up in an appropriate solvent, expecially dichloromethane, and filtered to remove any impurities. The product may then be purified by distillation or in the case of solids recrystallized from appropriate solvents.

C. Preparation of Sulfamates

An amino alcohol as prepared in Example 3 (1 mmol) and a suitable base, such as triethylamine, pyridine, sodium carbonate, and the like, preferably diisopropylethylamine (1 mmol) are dissolved in a suitable solvent such as ether, chloroform, acetonitrile and the like, but preferably dichloromethane. The sulfamoyl chloride from part A or B of Example 4, neat or dissolved in an appropriate solvent, is added to the above solution. The reaction is stirred at zero to reflux temperatures, but preferably at room temperature for 1 to 48 hours. The product can be purified by silica gel chromatography or by an extractive workup followed by recrystallization.

A representative compound prepared according to these general procedures is shown in the following Example.

EXAMPLE 15

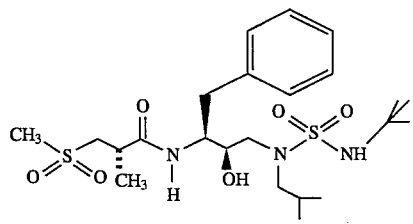

Preparation of
N-[3-[[[(1,1-dimethylethyl)amino]sulfonyl]
(2-methylpropyl)amino]-2R-hydroxy-
1S-(phenylmethyl)propyl]-2S-methyl-
3-(methylsulfonyl)propanamide To a solution of 52 mg (0.31 mmol) of 2(S)-methyl-3-(methylsulfonyl) propionic acid and 71 mg (0.46 mmol) N-hydroxybenzotriazole in 2 mL of N,N-dimethylformamide (DMF) at 0° C., was added 65 mg (0.34 mmol) of 1-(3-dimethylaminopropyl)-3-ethylcarbodiimide hydrochloride. After stirring at 0° C. for one hour, a solution of 104 mg (0.28 mmol) of free amine from Example 8, Part C in 1.5 mL of DMF was added. After two hours at 0° C. and sixteen hours at room temperature, the solvent was removed in vacuo, the residue dissolved in ethyl acetate and sequentially washed with saturated aqueous sodium bicarbonate, 5% aqueous citric acid, saturated sodium chloride, dired over anhydrous magnesium sulfate, filtered and concentrated to afford 140 mg of crude product. This was chromatographed on silica gel using 3%–5% isopropanol/methylene chloride to provide 45 mg of the desired product, m/e=520 (M+H).

Utilizing the procedures set forth above, the compounds shown in Tables 3–13 could be prepared. Thus, utilizing the intermediates of Examples 1–10 and coupling such intermediates to the sulfonyl alkanoyl compounds of Examples 11–14 according to the procedure illustrated by Example 15, the compounds shown in Tables 3–16 could be prepared.

TABLE 3

| Entry No. | R³ | R⁴ | R⁵ |
|---|---|---|---|
| 1 | CH₃ | n-Butyl | CH₃ |
| 2 | i-Butyl | CH₃ | C₆H₅ |
| 3 | i-Butyl | n-Butyl | CH₃ |
| 4 | i-Butyl | n-Butyl | H |
| 5 | i-Propyl | n-Butyl | H |
| 6 | i-Propyl | n-Butyl | CH₃ |
| 7 | C₆H₅ | n-Butyl | H |
| 8 | —CH₂—cyclohexyl | n-Butyl | H |
| 9 | —CH₂—phenyl | n-Butyl | CH₃ |

TABLE 3-continued

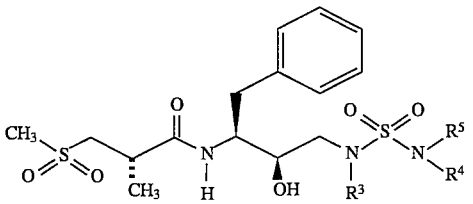

| Entry No. | R³ | R⁴ | R⁵ |
|---|---|---|---|
| 10 | —CH₂—C₆H₅ (benzyl) | n-Butyl | H |
| 11 | cyclohexyl | n-Butyl | CH₃ |
| 12 | i-Butyl | n-Propyl | CH₃ |
| 13 | i-Butyl | —CH₂CH(CH₃)₂ | CH₃ |
| 14 | (R)—CH(CH₃)—C₆H₅ | n-Butyl | CH₃ |
| 15 | CH₂-cyclohexyl | i-Propyl | CH₃ |
| 16 | —CH₂-cyclohexyl | —CH₂CH₂CH(CH₃)₂ | CH₃ |
| 17 | i-Butyl | —CH₂CH₃ | CH₃ |
| 18 | i-Butyl | —CH(CH₃)₂ | CH₃ |
| 19 | i-Butyl | cyclohexyl | CH₃ |
| 20 | -Butyl | cyclohexyl | H |
| 21 | —CH₂-cyclohexyl | —(CH₂)₂CH(CH₃)₂ | CH₃ |
| 22 | (CH₂)₂CH(CH₃)₂ | —CH(CH₃)₂ | CH₃ |
| 23 | i-Butyl | —CH(CH₃)₂ | H |
| 24 | i-Butyl | —C(CH₃)₃ | CH₃ |
| 25 | i-Butyl | —C(CH₃)₃ | H |
| 26 | —CH₂-naphthyl | —C(CH₃)₃ | CH₃ |
| 27 | —CH₂-naphthyl | —C(CH₃)₃ | H |
| 28 | —(CH₂)₂CH(CH₃)₂ | —C(CH₃)₃ | H |
| 29 | —(CH₂)₂CH(CH₃)₂ | —C(CH₃)₃ | CH₃ |
| 30 | —CH₂C₆H₅ | —C(CH₃)₃ | CH₃ |

TABLE 3-continued

Structure: CH₃-S(O)₂-CH₂-CH(CH₃)-C(O)-NH-CH(CH₂C₆H₅)-CH(OH)-CH₂-N(R³)-S(O)₂-N(R⁴)(R⁵)

| Entry No. | R³ | R⁴ | R⁵ |
|---|---|---|---|
| 31 | —CH₂C₆H₅ | —C(CH₃)₃ | H |
| 32 | —(CH₂)₂C₆H₅ | —C(CH₃)₃ | CH₃ |
| 33 | —(CH₂)₂C₆H₅ | —C(CH₃)₃ | H |
| 34 | n-Butyl | —C(CH₃)₃ | H |
| 35 | n-Pentyl | —C(CH₃)₃ | CH₃ |
| 36 | n-Hexyl | —C(CH₃)₃ | CH₃ |
| 37 | —CH₂—(C₆H₅, cyclohexadiene) | —C(CH₃)₃ | CH₃ |
| 38 | —CH₂C(CH₃)₃ | —C(CH₃)₃ | CH₃ |
| 39 | —CH₂C(CH₃)₃ | —C(CH₃)₃ | H |
| 40 | —CH₂CH₂—N(morpholino)O | —C(CH₃)₃ | H |
| 41 | —CH₂C₆H₅OCH₃ (para) | —C(CH₃)₃ | H |
| 42 | —CH₂—(3-pyridyl) | —C(CH₃)₃ | H |
| 43 | —CH₂—(4-pyridyl) | —C(CH₃)₃ | H |
| 44 | —(CH₂)₂C(CH₃)₃ | —C(CH₃)₃ | CH₃ |
| 45 | —(CH₂)₂C(CH₃)₃ | —C(CH₃)₃ | H |
| 46 | —(CH₂)₄OH | —C(CH₃)₃ | CH₃ |
| 47 | —(CH₂)₄OH | —C(CH₃)₃ | H |
| 48 | —CH₂—(4-F-C₆H₄) | —C(CH₃)₃ | H |
| 49 | —CH₂—(pyridyl) | —C(CH₃)₃ | CH₃ |
| 50 | —CH₂CH(CH₃)₂ | —C₆H₅ | CH₃ |
| 51 | —CH₂CH(CH₃)₂ | —C₆H₅ | H |
| 52 | —CH₂CH(CH₃)₂ | —C₆H₅ | —CH₂CH(CH₃)₂ |
| 53 | —CH₂Ph | —Ph | H |
| 54 | —CH₂—(4-F-C₆H₄) | —Ph | H |
| 55 | —CH₂—(cyclohexyl) | —Ph | H |

TABLE 3-continued

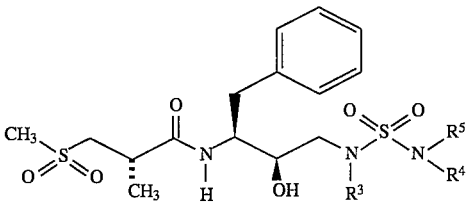

| Entry No. | R³ | R⁴ | R⁵ |
|---|---|---|---|
| 56 | —CH₂—⟨C₆H₄⟩—OCH₃ | —Ph | H |
| 57 | —CH₂—⟨4-pyridyl⟩ | —Ph | H |
| 58 | —CH₂—cyclopropyl | —Ph | H |
| 59 | —CH₂CH=CH₂ | —Ph | H |
| 60 | —Ph | —Ph | H |
| 61 | —cyclohexyl | —Ph | H |
| 62 | —CH₂CH₂Ph | —Ph | H |
| 63 | —CH₂CH₂CH₂OH | —Ph | H |
| 64 | —CH₂CH₂N(CH₃)₂ | —Ph | H |
| 65 | —CH₂CH₂—N(morpholino) | —Ph | H |
| 66 | —CH₃ | —Ph | H |
| 67 | —CH₂CH₂CH₂SCH₃ | —Ph | H |
| 68 | —CH₂CH₂CH₂S(O)₂CH₃ | —Ph | H |
| 69 | —CH₂CH₂CH₂CH(CH₃)₂ | —Ph | H |
| 70 | —CH₂CH₂CH(CH₃)₂ | —CH₂—Ph | H |
| 71 | —CH₂CH₂CH(CH₃)₂ | —CH₂CH₂CH₃ | H |
| 72 | —CH₂CH₂CH₂CH(CH₃)₂ | —CH₃ | H |
| 73 | —CH₂CH₂CH(CH₃)₂ | —C₆H₄—F | H |
| 74 | —CH₂CH₂CH(CH₃)₂ | —naphthyl | H |

TABLE 3-continued

[Structure: CH₃-S(O₂)-CH(CH₃)-C(O)-NH-CH(CH₂Ph)-CH(OH)-CH₂-N(R³)-S(O₂)-N(R⁴)(R⁵)]

| Entry No. | R³ | R⁴ | R⁵ |
|---|---|---|---|
| 75 | —CH₂CH₂CH(CH₃)₂ | 4-NO₂-phenyl | H |
| 76 | —CH₂CH₂CH(CH₃)₂ | 2-thienyl | H |
| 77 | —CH₂CH₂CH(CH₃)₂ | 4-OCH₃-phenyl | H |
| 78 | —CH₂CH₂CH(CH₃)₂ | 3-NO₂-phenyl | H |
| 79 | —CH₂CH₂CH(CH₃)₂ | 2-NO₂-phenyl | H |
| 80 | —CH₂CH₂CH(CH₃)₂ | 3-CF₃-phenyl | H |
| 81 | —CH₂CH₂CH(CH₃)₂ | 4-NHAc-phenyl | H |
| 82 | —CH₂CH₂CH(CH₃)₂ | 4-Cl-phenyl | H |
| 83 | —CH₂CH₂CH(CH₃)₂ | 4-CH₃-phenyl | H |
| 84 | —CH₂CH₂CH(CH₃)₂ | 2-CO₂CH₃-phenyl | H |
| 85 | —CH₂CH₂CH(CH₃)₂ | phenyl | H |

TABLE 3-continued
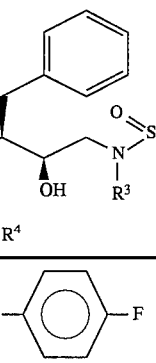
| Entry No. | R³ | R⁴ | R⁵ |
|---|---|---|---|
| 86 | —CH₂CH(CH₃)₂ | 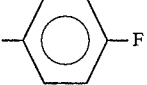 4-F-phenyl | H |
| 87 | —CH₂CH(CH₃)₂ | 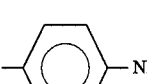 4-NHAc-phenyl | H |
| 88 | —CH₂CH(CH₃)₂ | 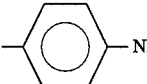 4-CH₃-phenyl | H |
| 89 | —CH₂CH₂CH₃ | 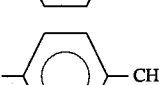 4-OCH₃-phenyl | H |
| 90 | —CH₂CH₂CH₂CH₃ |  4-OCH₃-phenyl | H |
| 91 | —CH₂CH₂CH₃ | 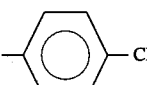 2-thienyl | H |
| 92 | —CH₂CH₂CH₃ | 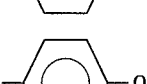 2-furyl | H |
| 93 | —CH₂CH₂CH₃ | 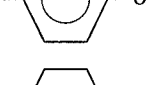 2-pyridyl | H |
| 94 | —CH₂CH₂CH₃ | 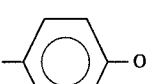 3-pyridyl | H |

TABLE 4

| Entry | R¹ | R⁴ |
|---|---|---|
| 1 | CH$_2$SO$_2$CH$_3$ | t-butyl |
| 2 | (R)—CH(OH)CH$_3$ | t-butyl |
| 3 | CH(CH$_3$)$_2$ | t-butyl |
| 4 | (R,S)CH$_2$SOCH$_3$ | t-butyl |
| 5 | CH$_2$SO$_2$NH$_2$ | t-butyl |
| 6 | CH$_2$SCH$_3$ | t-butyl |
| 7 | CH$_2$CH(CH$_3$)$_2$ | t-butyl |
| 8 | CH$_2$CH$_2$C(O)NH$_2$ | t-butyl |
| 9 | (S)—CH(OH)CH$_3$ | t-butyl |
| 10 | —CH$_2$C≡C—H | t-butyl |
| 11 | CH$_3$ | t-butyl |
| 12 | CH$_2$CH$_3$ | t-butyl |
| 13 | C(CH$_3$)$_3$ | t-butyl |

TABLE 5

| Entry | R | R² |
|---|---|---|
| 1 | —OCH$_3$ | n-Bu |
| 2 | —OCH$_3$ | cyclohexylmethyl |
| 3 | —NHA$_C$ | n-Bu |
| 4 | —NH$_2$ | n-Bu |
| 5 | —OCH$_3$ | C$_6$H$_5$CH$_2$ |
| 6 | —NHA$_C$ | C$_6$H$_5$CH$_2$ |
| 7 | —NH$_2$ | C$_6$H$_5$CH$_2$ |
| 8 | —NHA$_C$ | cyclohexylmethyl |
| 9 | —C(CH$_3$)$_3$ | n-Bu |
| 10 | —NH$_2$ | cyclohexylmethyl |
| 11 | —C(CH$_3$)$_3$ | C$_6$H$_5$CH$_2$ |
| 12 | —OCH$_3$ | 2-naphthylmethyl |
| 13 | —NHA$_C$ | 2-naphthylmethyl |
| 14 | —NH$_2$ | 2-naphthylmethyl |
| 15 | —C(CH$_3$)$_3$ | 2-naphthylmethyl |
| 16 | —OCH$_3$ | p-F(C$_6$H$_4$)CH$_2$ |
| 17 | —NH$_2$ | p-F(C$_6$H$_4$)CH$_2$ |
| 18 | —NHA$_C$ | p-F(C$_6$H$_4$)CH$_2$ |
| 19 | —C(CH$_3$)$_3$ | p-F(C$_6$H$_4$)CH$_2$ |
| 20 | —CF$_3$ | C$_6$H$_5$CH$_2$ |
| 21 | —CO$_2$CH$_3$ | C$_6$H$_5$CH$_2$ |
| 22 | —F | C$_6$H$_5$CH$_2$ |
| 23 | Cl | C$_6$H$_5$CH$_2$ |

TABLE 6

| Entry | R³ | R⁴ |
|---|---|---|
| 1 | —CH$_2$CH(CH$_3$)$_2$ | —C(CH$_3$)$_2$ |
| 2 | —CH$_2$CH$_2$CH(CH$_3$)$_2$ | cyclopropyl |
| 3 | —CH$_2$CH$_2$CH(CH$_3$)$_2$ | cyclobutyl |
| 4 | —CH$_2$CH$_2$CH(CH$_3$)$_2$ | cyclopentyl |
| 5 | —CH$_2$CH$_2$CH(CH$_3$)$_2$ | cyclohexyl |

TABLE 7

| Entry | R |
|---|---|
| 1 | CH$_3$— |
| 2 | CH$_3$CH$_2$— |
| 3 | CH$_3$CH$_2$CH$_2$— |
| 4 | PhCH$_2$CH$_2$— |
| 5 | PhCH$_2$— |
| 6 | Ph— |
| 7 | (CH$_3$)$_2$CH— |
| 8 | HOCH$_2$CH$_2$— |
| 9 | C$_6$H$_5$CH$_2$O—C(O)CH$_2$— |
| 10 | H$_2$NC(O)CH$_2$— |
| 11 | cyclohexyl |
| 12 | CH$_2$=CH—CH$_2$— |

TABLE 8

[Structure: CH₃-S(O)₂-CH₂-CH(CH₃)-C(O)-NH-CH(CH₂Ph)-CH(OH)-CH₂-N(R³)-S(O)₂-N(R⁴)(R⁵)]

| Entry | R³ | –NR⁴R⁵ |
|-------|----|----|
| 1 | CH₂CH(CH₃)₂ | pyrrolidinyl (N in 5-membered ring) |
| 2 | CH₂CH₂CH(CH₃)₂ | piperidinyl (N in 6-membered ring) |
| 3 | –CH₂–cyclohexyl | N in 7-membered ring (azepanyl) |
| 4 | cyclohexyl | N in 8-membered ring (azocanyl) |
| 5 | –CH(CH₃)₂ | morpholinyl |
| 6 | –CH₂–phenyl | N-methylpiperazinyl |

EXAMPLE 16

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 17. The enzyme method is described below. The substrate is 2-Ile-Nle-Phe(p-NO₂)-Gln-ArgNH₂. The positive control is MVT-101 (Miller, M. et al, *Science*, 246, 1149 (1989)] The assay conditions are as follows:

Assay buffer:
20 mM sodium phosphate, pH 6.4
20% glycerol
1 mM EDTA
1 mM DTT
0.1% CHAPS The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10x the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

The preceding examples can be repeated with similar success by substituting the generically or specifically described reactants and/or operating conditions of this invention for those used in the preceding examples.

TABLE 9

| Compound of Example No. | $IC_{50}$ (nanomolar) |
|---|---|
| 14 | 140 |

EXAMPLE 17

CEM Cell Assay

The effectiveness of the compounds can also be determined in a CEM cell assay.

The HIV inhibition assay method of acutely infected cells is an automated tetrazolium based colorimetric assay essentially that reported by Pauwles et al, *J. Virol. Methods*, 20, 309–321 (1988). Assays can be performed in 96-well tissue culture plates. CEM cells, a CD4⁺ cell line, were grown in RPMI-1640 medium (Gibco) supplemented with a 10% fetal calf serum and were then treated with polybrene (2 μg/ml). An 80 μl volume of medium containing 1×10⁴ cells is dispensed into each well of the tissue culture plate. To each well is added a 100 μl volume of zest compound dissolved in tissue culture medium (or medium without test compound as a control) to achieve the desired final concentration and the cells are incubated at 37° C. for 1 hour. A frozen culture of HIV-1 is diluted in culture medium to a concentration of 5×10⁴ $TCID_{50}$ per ml ($TCID_{50}$=the dose of virus that infects 50% of cells in tissue culture), and a 20 μL volume of the virus sample (containing 1000 $TCID_{50}$ of virus) is added to wells containing test compound and to wells containing only medium (infected control cells). Several wells receive culture medium without virus (uninfected control cells). Likewise, the intrinsic toxicity of the test compound is determined by adding medium without virus to several wells containing test compound. In summary, the tissue culture plates contain the following experiments:

| | Virus | Cells | Drug |
|---|---|---|---|
| 1. | + | – | – |
| 2. | + | + | – |
| 3. | + | – | + |
| 4. | + | + | + |

In experiments 2 and 4 the final concentrations of test compounds are 1, 10, 100 and 500 μg/ml. Either azidothymidine (AZT) or dideoxyinosine (ddI) is included as a positive drug control. Test compounds are dissolved in DMSO and diluted into tissue culture medium so that the final DMSO concentration does not exceed 1.5% in any case. DMSO is added to all control wells at an appropriate concentration.

Following the addition of virus, cells are incubated at 37° C. in a humidified, 5% $CO_2$ atmosphere for 7 days. Test compounds could be added on days 0, 2 and 5 if desired. On day 7, post-infection, the cells in each well are resuspended and a 100 µl sample of each cell suspension is removed for assay. A 20 µL volume of a 5 mg/ml solution of 3-(4,5-dimethylthiazol-2-yl)-2,5-diphenyltetrazolium bromide (MTT) is added to each 100 µL cell suspension, and the cells are incubated for 4 hours at 27° C. in a 5% $CO_2$ environment. During this incubation, MTT is metabolically reduced by living cells resulting in the production in the cell of a colored formazan product. To each sample is added 100 µl of 10% sodium dodecylsulfate in 0.01N HCl to lyse the cells, and samples are incubated overnight. The absorbance at 590 nm is determined for each sample using a Molecular Devices microplate reader. Absorbance values for each set of wells is compared to assess vital control infection, uninfected control cell response as well as test compound by cytotoxicity and antiviral efficacy.

The biological data shown in Table 10 was obtained from the compounds shown in Table 1C.

TABLE 10

| Biological Data: Table 1C | | | |
|---|---|---|---|
| Entry: | IC50 or % inhibition | EC50 | TD50 |
| A | 29% @ 0.1 uM | | |
| B | 55% @ 10.0 uM | | |
| C | 59% @ 1.0 uM | | |
| D | 29% @ 0.1 uM | | |
| E | 70 nM | 880 nM | 7.5 uM |
| F | 22% @ 0.1 uM | | |
| G | 66 nM | | |
| H | 48% @ 10.0 uM | | |
| I | 1.7 uM | | |
| J | 2.69 uM | | |
| K | 60% @ 10.0 uM | | |
| L | 38% @ 10.0 uM | | |
| M | NT | | |

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in. particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 50 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or search. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound represented by the formula

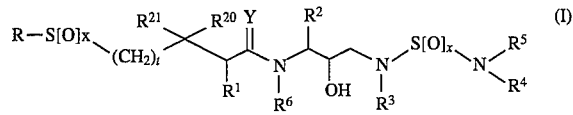

or a pharmaceutically acceptable salt, or ester thereof wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, aralkoxyalkyl, heteroaryl, aralkyl, heteroalkyl, heteroaralkyl, aminocarbonylalkyl, aminoalkyl, aminoalkylcarbonylalkyl, alkylcarbonylalkyl, aryloxyalkylcarbonyl, and aralkoxycarbonylalkyl radicals, aminoalkyl, and mono- and disubstituted aminoalkyl, mono- and disubstituted aminocarbonylalkyl and mono- and disubstituted aminoalkanoylalkyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or wherein said aminoalkyl, aminocarbonylalkyl and aminoalkanoylalkyl radicals are disubstituted, said substituents along with the nitrogen atom to which they are attached form a heterocycloalkyl or heteroaryl radical;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials, $-NO_2$, $-CN$, $-CF_3$, $-OR^9$ and $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroalkyl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ and $R^5$ independently represent hydrogen and radicals as defined by $R^3$ or together with a nitrogen atom to which they are bonded form a heterocycloalkyl or a heteroaryl radical;

$R^6$ represents hydrogen and alkyl radicals;

each x independently represents 1 or 2;

t represents either 0, 1 or 2; and

Y represents O, S and $NR^{15}$ wherein $R^{15}$ represents hydrogen and radicals as defined for $R^3$.

2. A compound represented by Formula II:

$$\text{R}-\underset{(CH_2)_t}{\overset{O}{\underset{\|}{S}}}\overset{O}{\underset{\|}{\|}}-\underset{R^1}{\overset{R^{21}}{\underset{|}{C}}}-\underset{}{\overset{R^{20}}{\underset{|}{C}}}-\overset{O}{\underset{\|}{C}}-NH-\underset{OH}{\overset{R^2}{\underset{|}{C}}}-CH_2-\underset{R^3}{\overset{}{\underset{|}{N}}}-\underset{R^4}{\overset{O}{\underset{\|}{S}}}\overset{O}{\underset{\|}{\|}}-N-R^5 \quad (II)$$

wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminoalkyl, aralkoxyalkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, -CH$_2$SO$_2$NH$_2$, -CH$_2$CO$_2$CH$_3$, -CO$_2$CH$_3$, -CONH$_2$, -CH$_2$C(O)NHCH$_3$, -C(CH$_3$)$_2$(SH), -C(CH$_3$)$_2$(SCH$_3$), -C(CH$_3$)$_2$(S[O]CH$_3$), -C(CH$_3$)$_2$(S[O]$_2$CH$_3$), alkyl, haloalkyl, alkenyl, alkynyl and cycloalkyl radicals, and amino acid side chains selected from asparagine, S-methyl cysteine and methionine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials, -NO$_2$, -C$\equiv$N, CF$_3$, -OR$^9$, -SR$^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ and $R^5$ independently represent hydrogen and radicals as defined by $R^3$, or together with the nitrogen atom to which they are bonded represent heterocycloalkyl and heteroaryl radicals; and t represents 0 or 1.

3. A compound of claim 2 wherein R represents alkyl, aryl and aralkyl radicals.

4. A compound of claim 2 wherein R represents methyl and phenethyl radicals.

5. A compound of claim 2 wherein $R^1$, $R^{20}$ and $R^{21}$ independently represent hydrogen CH$_2$C(O)NHCH$_3$, C(CH$_3$)$_2$(SCH$_3$), C(CH$_3$)$_2$(S[O]CH$_3$), C(CH$_3$)$_2$(S[O]$_2$CH$_3$), alkyl, alkenyl, alkynyl and cycloalkyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine.

6. A compound of claim 2 wherein $R^1$, $R^{20}$ and $R^{21}$ independently represent hydrogen, CH$_2$C(O)NHCH$_3$, C(CH$_3$)$_2$(SCH$_3$), C(CH$_3$)$_2$(S[O]CH$_3$), C(CH$_3$)$_2$(S[O]$_2$CH$_3$), methyl, propargyl, t-butyl, isopropyl and sec-butyl radicals, and amino acid side chains selected from the group consisting of asparagine, valine, S-methyl cysteine, allo-iso-leucine, iso-leucine, and beta-cyano alanine side chains.

7. A compound of claim 2 wherein $R^1$ $R^{20}$ and $R^{21}$ independently represent hydrogen and methyl, ethyl, propartyl, t-butyl, isopropyl and sec-butyl radicals.

8. A compound of claim 2 wherein $R^2$ represents alkyl, cycloalkylalkyl and aralkyl radicals, which radicals are optionally substituted with halogen radicals and radicals represented by the formula -OR$^9$ and -SR$^9$ wherein $R^9$ represents hydrogen and alkyl radicals.

9. A compound of claim 2 wherein $R^2$ represents alkyl, cycloalkylalkyl and aralkyl radicals.

10. A compound of claim 2 wherein $R^2$ represents CH$_3$SCH$_2$CH$_2$-, iso-butyl, n-butyl, benzyl, 4-fluorobenzyl, 2-naphthylmethyl and cyclohexylmethyl radicals.

11. A compound of claim 2 wherein $R^3$ represents alkyl, haloalkyl, alkenyl, alkoxyalkyl, cycloalkyl, cycloalkylalkyl, heterocycloalkyl, heterocycloalkylalkyl, aryl, aralkyl and heteroaralkyl radicals.

12. A compound of claim 2 wherein $R^5$ is hydrogen and $R^3$ represents alkyl, cycloalkyl, cycloalkylalkyl, aralkyl, heteroaralkyl, heterocycloalkyl, heterocycloalkylalkyl radicals.

13. A compound of claim 2 wherein $R^3$ represents alkyl, heterocycloalkyl and heterocycloalkylalkyl radicals.

14. A compound of claim 2 wherein $R^3$ represents isobutyl, n-propyl, isopropyl, n-butyl, isoamyl, cyclohexyl, cyclohexylmethyl, benzyl and pyridylmethyl radicals.

15. A compound of claim 2 wherein $R^5$ is hydrogen, $R^3$ is a isobutyl or isoamyl radical and $R^4$ is a tertiary-butyl radical.

16. A compound of claim 2 wherein $R^5$ is hydrogen, $R^3$ is a cyclohexyl or cyclohexylmethyl radical and $R^4$ is a tertiary-butyl radical.

17. A compound of claim 2 wherein $R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals.

18. A compound of claim 2 wherein $R^4$ and $R^5$ independently represent hydrogen, alkyl and aryl radicals.

19. A compound of claim 2 wherein $R^4$ and $R^5$ independently represent hydrogen, methyl, ethyl, isopropyl, propyl, n-butyl, t-butyl, 1,1-dimethylpropyl, cyclohexyl and phenyl radicals.

20. A compound of claim 2 wherein $R^4$ and $R^5$ together with the nitrogen atom to which they are bonded form a heterocyloalkyl or heteroaryl radical.

21. A compound of claim 2 wherein $R^4$ and $R^5$ together with the nitrogen atom to which they are bonded form a heterocycloalkyl or heteroaryl radical having from 4 to 8 ring members.

22. A compound of claim 2 wherein $R^4$ and $R^5$ together with the nitrogen atom to which they are bonded form a pyrrolidinyl, piperidinyl, morpholinyl, piperazinyl or N-alkylpiperazinyl radical.

23. A pharmaceutical composition comprising an effective amount of a compound of claim 1 and a pharmaceutically acceptable carrier.

24. A pharmaceutical composition comprising an effective amount of a compound of claim 2 and a pharmaceutically acceptable carrier.

25. A method of inhibiting a retroviral protease comprising administering a protease inhibiting amount of a composition of claim 23.

26. The method of claim 25 wherein the retroviral protease is HIV protease.

27. A method of treating a retroviral infection comprising administering an effective amount of a composition of claim 23.

28. The method of claim 27 wherein the retroviral infection is an HIV infection.

29. A method for treating AIDS comprising administering an effective amount of a composition of claim 23.

30. A method of inhibiting a retroviral protease comprising administering a protease inhibiting amount of a composition of claim 24.

31. The method of claim 30 wherein the retroviral protease is HIV protease.

32. A method of treating a retroviral infection comprising administering an effective amount of a composition of claim 24.

33. The method of claim 30 wherein the retroviral infection is an HIV infection.

34. A method for treating AIDS comprising administering an effective amount of a composition of claim 24.

35. A compound represented by Formula III:

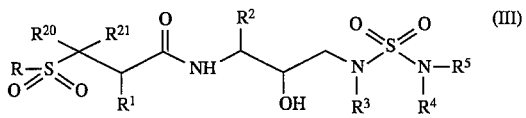

wherein:

R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aralkoxyalkyl, aminoalkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$ derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C\equiv N$, $CF_3$, $-OR^9$, $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof; and $R^4$ and $R^5$ independently represent hydrogen and radicals as defined for $R^3$ or together with a nitrogen atom to which they are bonded form a heterocycloalkyl or a heteroaryl radical.

36. A compound of claim 35 wherein R represents alkyl, aryl and aralkyl radicals.

37. A compound of claim 35 wherein R represents methyl and phenethyl.

38. A compound of claim 35 wherein $R^1$, $R^{20}$ and $R^{21}$ independently represent hydrogen, $CH_2C(O)NHCH_3$, $C(CH_3)_2(SCH_3)$, $C(CH_3)_2(S[O]CH_3)$, $C(CH_3)_2(S[O]_2CH_3)$, alkyl, alkenyl, alkynyl and cycloalkyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine.

39. A compound of claim 35 wherein $R^1$, $R^{20}$ and $R^{21}$ independently represent hydrogen $CH_2C(O)NHCH_3$, $C(CH_3)_2(SCH_3)$, $C(CH_3)_2(S[O]CH_3)$, $C(CH_3)_2(S[O]_2CH_3)$, methyl, ethyl, propargyl, t-butyl, isopropyl and sec-butyl radicals, and amino acid side chains selected from the group consisting of asparagine, valine, S-methyl cysteine, allo-isoleucine, iso-leucine, and beta-cyano alanine side chains.

40. A compound of claim 35 wherein $R^1$, $R^{20}$ and $R^{21}$ independently represent hydrogen, methyl, ethyl, propargyl, t-butyl, isopropyl and sec-butyl radicals, and amino acid side chains selected from the group consisting of asparagine, valine, S-methyl cysteine, methionine, allo-iso-leucine, iso-leucine, threonine, serine, aspartic acid, beta-cyano alanine, and allo-threonine side chains.

41. A compound of claim 35 wherein $R^1$, $R^{20}$ and $R^{21}$ independently represent hydrogen and methyl, ethyl, propargyl, t-butyl, isopropyl and sec-butyl radicals.

42. A compound of claim 35 wherein $R^2$ represents alkyl, cycloalkylalkyl and aralkyl radicals, which radicals are optionally substituted with halogen radicals and radicals represented by the formula $-OR^9$ and $-SR^9$ wherein $R^9$ represents hydrogen and alkyl radicals.

43. A compound of claim 35 wherein $R^2$ represents alkyl, cycloalkylalkyl and aralkyl radicals.

44. A compound of claim 35 wherein $R^2$ represents $CH_3SCH_2CH_2-$, iso-butyl, n-butyl, benzyl, 4-fluorobenzyl, 2-naphthylmethyl and cyclohexylmethyl radicals.

45. A compound of claim 35 wherein $R^2$ represents benzyl, 4-fluorobenzyl, and 2-naphthylmethyl radicals.

46. A compound of claim 35 wherein $R^3$ independently represents alkyl, haloalkyl, alkenyl, alkynyl, alkoxyalkyl, cycloalkyl, cycloalkylalkyl, hydroxyalkyl, heterocycloalkyl, heterocycloalkylalkyl, aryl, aralkyl and heteroaralkyl radicals.

47. A compound of claim 35 wherein $R^3$ represents alkyl, cycloalkyl, cycloalkylalkyl, aralkyl, heteroaralkyl, heterocycloalkyl, heterocycloalkylalkyl radicals.

48. A compound of claim 35 wherein $R^3$ represents isobutyl, n-propyl, isopropyl, n-butyl, isoamyl, cyclohexyl, cyclohexylmethyl, benzyl and pyridylmethyl radicals.

49. A compound of claim 35 wherein $R^5$ is hydrogen and $R^3$ and $R^4$ independently represent alkyl, heterocycloalkyl and heterocycloalkylalkyl radicals.

50. A compound of claim 35 wherein $R^5$ is hydrogen, $R^3$ is a isobutyl or isoamyl radical and $R^4$ is a tertiary-butyl radical.

51. A compound of claim 35 wherein $R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals.

52. A compound of claim 35 wherein $R^4$ and $R^5$ independently represent hydrogen, alkyl and aryl radicals.

53. A compound of claim 35 wherein $R^4$ and $R^5$ independently represent hydrogen, methyl, ethyl, propyl, isopropyl, n-butyl, t-butyl, 1,1-dimethylpropyl, cyclohexyl and phenyl radicals.

54. A compound of claim 35 wherein $R^4$ and $R^5$ together with the nitrogen atom to which they are bonded form a heterocyloalkyl or heteroaryl radical.

55. A compound of claim 35 wherein $R^4$ and $R^5$ together with the nitrogen atom to which they are bonded form a heterocycloalkyl or heteroaryl radical having from 4 to 8 ring members.

56. A compound of claim 35 wherein $R^4$ and $R^5$ together with the nitrogen atom to which they are bonded form a pyrrolidinyl, piperidinyl, morpholinyl, piperazinyl or N'-alkylpiperazinyl radical.

57. A pharmaceutical composition comprising an effective amount of a compound of claim 35 and a pharmaceutically acceptable carrier.

58. A method of inhibiting a retroviral protease comprising administering a protease inhibiting amount of a composition of claim 57.

59. The method of claim 58 wherein the retroviral protease is HIV protease.

60. A method of treating a retroviral infection comprising administering an effective amount of a composition of claim 57.

61. The method of claim 60 wherein the retroviral infection is an HIV infection.

62. A method for treating AIDS comprising administering an effective amount of a composition of claim 57.

63. A compound represented by the formula:

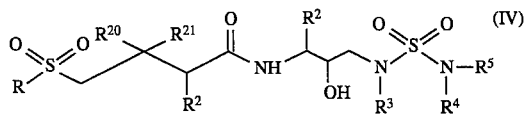

wherein R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aralkoxyalkyl, aminoalkyl, aminocarbonylalkyl, aminoalkylcarbonylalkyl, alkylcarbonylalkyl, aryloxyalkylcarbonylalkyl and aralkoxycarbonylalkyl radicals;

$R^1$, $R^{20}$ and $R^{21}$ independently represent hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains, or $R^{21}$ is hydrogen and $R^1$ and $R^{20}$ together with the carbon atoms to which they are attached form a three to six-membered cycloalkyl radical;

$R^2$ represents alkyl, aryl, cycloalkyl, cycloalkylalkyl and aralkyl radicals, which radicals are optionally substituted with a group selected from alkyl and halogen radicals, $-NO_2$, $-C\equiv N$, $CF_3$, $-OR^9$ and $-SR^9$, wherein $R^9$ represents hydrogen and alkyl radicals;

$R^3$ represents alkyl, haloalkyl, alkenyl, alkynyl, hydroxyalkyl, alkoxyalkyl, aryloxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl and the sulfone and sulfoxide derivatives thereof; and $R^4$ and $R^5$ independently represent hydrogen and radicals as defined by $R^3$, or together with the nitrogen atom to which they are bonded represent heterocycloalkyl and heteroaryl radicals.

64. A compound of claim 63 wherein R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroalkyl, heteroaralkyl, aminocarbonylalkyl, aminoalkyl, aminoalkylcarbonylalkyl, alkylcarbonylalkyl, aryloxyalkylcarbonylalkyl and aralkoxycarbonylalkyl radicals.

65. A compound of claim 63 wherein R represents alkyl, alkenyl, alkynyl, cycloalkyl, hydroxyalkyl, cycloalkylalkyl, heterocycloalkyl, heterocycloalkylalkyl, alkoxyalkyl, aryl, heteroaryl, aralkyl, heteroaralkyl, aminocarbonylalkyl, aminoalkylcarbonylalkyl, alkylcarbonylalkyl, aryloxyalkylcarbonylalkyl and aralkoxycarbonylalkyl radicals.

66. A compound of claim 63 wherein R represents methyl and phenethyl radicals.

67. A compound of claim 63 wherein $R^1$, $R^{20}$ and $R^{21}$ independently represent hydrogen and alkyl radicals having from 1 to about 4 carbon atoms, alkenyl, alkynyl and aralkyl radicals and radicals selected from $-CH_2SO_2NH_2$, $-CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SCH_3)$, $-C(CH_3)_2(S[O]CH_3)$ and $-C(CH_3)_2(S[O]_2CH_3)$.

68. A compound of claim 63 wherein $R^1$, $R^{20}$ and $R^{21}$ independently represent hydrogen, methyl, ethyl, isopropyl, propargyl and tertiary butyl radicals.

69. A compound of claim 63 wherein $R^{20}$ and $R^{21}$ are both hydrogen and $R^1$ is methyl.

70. A compound of claim 63 wherein $R^1$ and $R^{20}$ are both hydrogen and $R^{21}$ is methyl.

71. A compound of claim 63 wherein $R^1$ is hydrogen and $R^{20}$ and $R^{21}$ are both methyl.

72. A compound of claim 63 wherein $R^1$, $R^{20}$ and $R^{21}$ are each methyl.

73. A compound of claim 63 wherein $R^1$ is methyl, one of $R^{20}$ and $R^{21}$ is methyl and the other is hydrogen.

74. A compound of claim 63 wherein $R^2$ represents alkyl, cycloalkylalkyl and aralkyl radicals, which radicals are optionally substituted with halogen radicals and radicals represented by the formula $-OR^9$ and $-SR^9$ wherein $R^9$ represents hydrogen and alkyl radicals.

75. A compound of claim 63 wherein $R^2$ represents alkyl, cycloalkylalkyl and aralkyl radicals.

76. A compound of claim 63 wherein $R^2$ represents aralkyl radicals.

77. A compound of claim 63 wherein $R^3$ independently represents alkyl, haloalkyl, alkenyl, alkoxyalkyl, cycloalkyl, cycloalkylalkyl, heterocycloalkyl, heterocycloalkylalkyl, aryl, aralkyl and heteroaralkyl radicals.

78. A compound of claim 63 wherein $R^3$ represents alkyl, cycloalkyl, cycloalkylalkyl, aralkyl, heteroaralkyl, heterocycloalkyl, heterocycloalkylalkyl radicals.

79. A compound of claim 63 wherein $R^3$ represents alkyl, heterocycloalkyl and heterocycloalkylalkyl radicals.

80. A compound of claim 63 wherein $R^3$ represents isobutyl, n-propyl, isopropyl, n-butyl, isoamyl, cyclohexyl, cyclohexylmethyl, benzyl and pyridylmethyl radicals.

81. A compound of claim 63 wherein $R^5$ is hydrogen, $R^3$ is a isobutyl or isoamyl radical and $R^4$ is a tertiary-butyl radical.

82. A compound of claim 63 wherein $R^5$ is hydrogen, $R^3$ is a cyclohexyl or cyclohexylmethyl radical and $R^4$ is a tertiary-butyl radical.

83. A compound of claim 63 wherein $R^4$ and $R^5$ independently represent hydrogen, alkyl, cycloalkyl, cycloalkylalkyl, aryl, heteroaryl, aralkyl, heteroaralkyl, heterocycloalkyl and heterocycloalkylalkyl radicals.

84. A compound of claim 63 wherein $R^4$ and $R^5$ independently represent hydrogen, alkyl and aryl radicals.

85. A compound of claim 63 wherein $R^4$ and $R^5$ independently represent hydrogen, methyl, ethyl, propyl, isopropyl, n-butyl, t-butyl, 1,1-dimethylpropyl, cyclohexyl and phenyl radicals.

86. A compound of claim 63 wherein $R^4$ and $R^5$ together with the nitrogen atom to which they are bonded form a heterocyloalkyl or heteroaryl radical.

87. A compound of claim 63 wherein $R^4$ and $R^5$ together with the nitrogen atom to which they are bonded form a heterocycloalkyl or heteroaryl radical having from 4 to 8 ring members.

88. A compound of claim 63 wherein $R^4$ and $R^5$ together with the nitrogen atom to which they are bonded form a pyrrolidinyl, piperidinyl, morpholinyl, piperazinyl or N'-alkylpiperazinyl radical.

89. A pharmaceutical composition comprising a compound of claim 63 and a pharmaceutically acceptable carrier.

90. A method of inhibiting a retroviral protease comprising administering a protease inhibiting amount of a composition of claim 89.

91. The method of claim 90 wherein the retroviral protease is HIV protease.

92. A method of treating a retroviral infection comprising administering an effective amount of a composition of claim 89.

93. The method of claim 92 wherein the retroviral infection is an HIV infection.

94. A method for treating AIDS comprising administering an effective amount of a composition of claim 89.

* * * * *